United States Patent
Matassa et al.

(10) Patent No.: US 6,867,284 B1
(45) Date of Patent: Mar. 15, 2005

(54) PEPTIDE INHIBITORS OF HEPATITIS C VIRUS NS3 PROTEASE

(75) Inventors: Victor Matassa, Vellehi (IT); Frank Narjes, Ariccia (IT); Konrad Forster Koehler, Huddinge (SE); Jesus Ontoria, Barcelona (ES); Marco Poma, Monte Argentario (IT); Antonella Marchetti, Cascia (IT)

(73) Assignee: Istituto di Ricerche di Biologia Molecolare P. Angeletti S.p.A., Pomezia (IT)

( * ) Notice: Subject to any disclaimer, the term of this patent is extended or adjusted under 35 U.S.C. 154(b) by 0 days.

(21) Appl. No.: 09/719,261

(22) PCT Filed: Jun. 9, 1999

(86) PCT No.: PCT/GB99/01824

§ 371 (c)(1),
(2), (4) Date: Jul. 23, 2001

(87) PCT Pub. No.: WO99/64442

PCT Pub. Date: Dec. 16, 1999

(30) Foreign Application Priority Data

Jun. 10, 1998 (GB) ................................ 9812523

(51) Int. Cl.⁷ ...................... A61K 38/04; C07K 17/00; C07K 16/00; C07K 7/00; C07K 5/00
(52) U.S. Cl. ...................... 530/329; 514/12; 530/330; 530/331; 530/332
(58) Field of Search .................... 514/12, 16, 18, 514/362, 383; 530/350, 329, 330, 331, 332; 548/128, 268.2, 131, 136

(56) References Cited

FOREIGN PATENT DOCUMENTS

| WO | WO 97/36587 | 10/1997 |
|---|---|---|
| WO | WO 97/43310 | 11/1997 |
| WO | WO 98/17679 | 4/1998 |
| WO | WO 98/22496 | 5/1998 |

OTHER PUBLICATIONS

E. Hoss, Peptide modification by incorporation of alpha–tifluoromethyl alpha–amino acids via tifluoromethyl–substituted *acylimines*, 1993, vol. 61, pp. 163–170.*

Ingallinella, P. et al. "Potent Peptide Inhibitors of Human Hepatitis C Virus NS3 Protease Are Obtained by Optimizing the Cleavage Products", Biochemistry, 1998, vol. 37, pp. 8906–8914.

Steinkuhler, C. et al. "Product Inhibition of the Hepatitis C Virus NS3 Protease", Biochemistry, 1998, vol. 37, pp. 8899–8905.

* cited by examiner

*Primary Examiner*—Robert A. Wax
*Assistant Examiner*—Robert B. Mondesi
(74) *Attorney, Agent, or Firm*—Sheldon O. Heber; Jack L. Tribble

(57) ABSTRACT

Fluorinated oligopeptides, especially those having 4,4-difluoro-2-amino butyric acid at the C terminus, may be effective inhibitors of hepatitis C virus NS3 protease. Examples of hexapeptides of the invention, optimized for binding in the S1 specificity pocket of the enzyme, may display $IC_{50}$s at the sub-micromolar level. Embodiments of tripeptides of the invention, having a keto-acid group at the C-terminus are, likewise, potent inhibitors of NS3 protease.

29 Claims, No Drawings

SEQUENCE LISTING

<160> NUMBER OF SEQ ID NOS: 13

<210> SEQ ID NO 1
<211> LENGTH: 4
<212> TYPE: PRT
<213> ORGANISM: Artificial Sequence
<220> FEATURE:
<221> NAME/KEY: SITE
<222> LOCATION: (1)
<223> OTHER INFORMATION: Xaa is diphenylalanine
<220> FEATURE:
<221> NAME/KEY: SITE
<222> LOCATION: (3)
<223> OTHER INFORMATION: Xaa is cyclohexylalanine
<220> FEATURE:
<221> NAME/KEY: SITE
<222> LOCATION: (4)
<223> OTHER INFORMATION: Xaa is 4,4-difluoro-2-amino butyric acid
<220> FEATURE:
<223> OTHER INFORMATION: Description of Artificial Sequence: Synthetic
      sequence

<400> SEQUENCE: 1

Xaa Glu Xaa Xaa
  1

<210> SEQ ID NO 2
<211> LENGTH: 6
<212> TYPE: PRT
<213> ORGANISM: Artificial Sequence
<220> FEATURE:
<221> NAME/KEY: SITE
<222> LOCATION: (6)
<223> OTHER INFORMATION: Xaa is 4,4-difluoro-2-amino butyric acid
<220> FEATURE:
<223> OTHER INFORMATION: Description of Artificial Sequence: Synthetic
      sequence

<400> SEQUENCE: 2

Asp Glu Met Glu Glu Xaa
  1               5

<210> SEQ ID NO 3
<211> LENGTH: 6
<212> TYPE: PRT
<213> ORGANISM: Artificial Sequence
<220> FEATURE:
<221> NAME/KEY: SITE
<222> LOCATION: (3)
<223> OTHER INFORMATION: Xaa is diphenylalanine
<220> FEATURE:
<221> NAME/KEY: SITE
<222> LOCATION: (5)
<223> OTHER INFORMATION: Xaa is cyclohexylalanine
<220> FEATURE:
<221> NAME/KEY: SITE
<222> LOCATION: (6)
<223> OTHER INFORMATION: Xaa is 4,4-difluoro-2-amino butyric acid
<220> FEATURE:
<223> OTHER INFORMATION: Description of Artificial Sequence: Synthetic
      sequence

<400> SEQUENCE: 3

Asp Glu Xaa Glu Xaa Xaa
  1               5

<210> SEQ ID NO 4
<211> LENGTH: 6
<212> TYPE: PRT
<213> ORGANISM: Artificial Sequence

```
<220> FEATURE:
<221> NAME/KEY: SITE
<222> LOCATION: (3)
<223> OTHER INFORMATION: Xaa is diphenylalanine
<220> FEATURE:
<221> NAME/KEY: SITE
<222> LOCATION: (5)
<223> OTHER INFORMATION: Xaa is cyclohexylalanine
<220> FEATURE:
<221> NAME/KEY: SITE
<222> LOCATION: (6)
<223> OTHER INFORMATION: Xaa is a any amino acid
<220> FEATURE:
<221> NAME/KEY: MOD_RES
<222> LOCATION: (6)
<223> OTHER INFORMATION: fluorinated hydrocarbon side chain
<220> FEATURE:
<223> OTHER INFORMATION: Description of Artificial Sequence: Synthetic
      sequence

<400> SEQUENCE: 4

Asp Glu Xaa Glu Xaa Xaa
 1               5

<210> SEQ ID NO 5
<211> LENGTH: 6
<212> TYPE: PRT
<213> ORGANISM: Artificial Sequence
<220> FEATURE:
<221> NAME/KEY: SITE
<222> LOCATION: (6)
<223> OTHER INFORMATION: Xaa is a any amino acid
<220> FEATURE:
<221> NAME/KEY: MOD_RES
<222> LOCATION: (6)
<223> OTHER INFORMATION: fluorinated hydrocarbon side chain
<220> FEATURE:
<223> OTHER INFORMATION: Description of Artificial Sequence: Synthetic
      sequence

<400> SEQUENCE: 5

Asp Glu Met Glu Glu Xaa
 1               5

<210> SEQ ID NO 6
<211> LENGTH: 5
<212> TYPE: PRT
<213> ORGANISM: Artificial Sequence
<220> FEATURE:
<221> NAME/KEY: SITE
<222> LOCATION: (1)
<223> OTHER INFORMATION: Asp as tertiary butyl ester
<220> FEATURE:
<221> NAME/KEY: SITE
<222> LOCATION: (2, 4, 5)
<223> OTHER INFORMATION: Glu as tertiary butyl ester
<220> FEATURE:
<223> OTHER INFORMATION: Description of Artificial Sequence: Synthetic
      sequence

<400> SEQUENCE: 6

Asp Glu Met Glu Glu
 1               5

<210> SEQ ID NO 7
<211> LENGTH: 5
<212> TYPE: PRT
<213> ORGANISM: Artificial Sequence
<220> FEATURE:
<221> NAME/KEY: SITE
<222> LOCATION: (1)
<223> OTHER INFORMATION: Asp as tertiary butyl ester
<220> FEATURE:
```

```
<221> NAME/KEY: SITE
<222> LOCATION: (2, 4)
<223> OTHER INFORMATION: Glu as tertiary butyl ester
<220> FEATURE:
<221> NAME/KEY: SITE
<222> LOCATION: (3)
<223> OTHER INFORMATION: Xaa is diphenylalanine
<220> FEATURE:
<221> NAME/KEY: SITE
<222> LOCATION: (5)
<223> OTHER INFORMATION: Xaa is cyclohexylalanine
<220> FEATURE:
<223> OTHER INFORMATION: Description of Artificial Sequence: Synthetic
      sequence

<400> SEQUENCE: 7

Asp Glu Xaa Glu Xaa
  1               5

<210> SEQ ID NO 8
<211> LENGTH: 17
<212> TYPE: PRT
<213> ORGANISM: Artificial Sequence
<220> FEATURE:
<221> NAME/KEY: MOD_RES
<222> LOCATION: (17)
<223> OTHER INFORMATION: AMIDATION
<220> FEATURE:
<223> OTHER INFORMATION: Description of Artificial Sequence: Synthetic
      sequence

<400> SEQUENCE: 8

Lys Lys Lys Gly Ser Val Val Ile Val Gly Arg Ile Ile Leu Ser Gly
  1               5                  10                  15

Arg

<210> SEQ ID NO 9
<211> LENGTH: 13
<212> TYPE: PRT
<213> ORGANISM: Artificial Sequence
<220> FEATURE:
<223> OTHER INFORMATION: Description of Artificial Sequence: Synthetic
      sequence

<400> SEQUENCE: 9

Asp Glu Met Glu Glu Cys Ala Ser His Leu Pro Tyr Lys
  1               5                  10

<210> SEQ ID NO 10
<211> LENGTH: 4
<212> TYPE: PRT
<213> ORGANISM: Artificial Sequence
<220> FEATURE:
<221> NAME/KEY: SITE
<222> LOCATION: (1)..(3)
<223> OTHER INFORMATION: Phenylalanines are linked by an ether bond
<220> FEATURE:
<221> NAME/KEY: SITE
<222> LOCATION: (4)
<223> OTHER INFORMATION: Xaa is 4,4-difluoro-2-amino butyric acid
<220> FEATURE:
<223> OTHER INFORMATION: Description of Artificial Sequence: Synthetic
      sequence

<400> SEQUENCE: 10

Phe Glu Phe Xaa
  1

<210> SEQ ID NO 11
<211> LENGTH: 6
```

```
<212> TYPE: PRT
<213> ORGANISM: Artificial Sequence
<220> FEATURE:
<221> NAME/KEY: SITE
<222> LOCATION: (3)
<223> OTHER INFORMATION: Xaa is diphenylalanine
<220> FEATURE:
<221> NAME/KEY: SITE
<222> LOCATION: (5)
<223> OTHER INFORMATION: Xaa is cyclohexylalanine
<220> FEATURE:
<221> NAME/KEY: SITE
<222> LOCATION: (6)
<223> OTHER INFORMATION: Xaa is 3-amino-5,5-difluoro-pentanoic acid
<220> FEATURE:
<223> OTHER INFORMATION: Description of Artificial Sequence: Synthetic
      sequence

<400> SEQUENCE: 11

Asp Glu Xaa Glu Xaa Xaa
  1               5

<210> SEQ ID NO 12
<211> LENGTH: 5
<212> TYPE: PRT
<213> ORGANISM: Artificial Sequence
<220> FEATURE:
<221> NAME/KEY: SITE
<222> LOCATION: (2)
<223> OTHER INFORMATION: Xaa is diphenylalanine
<220> FEATURE:
<221> NAME/KEY: SITE
<222> LOCATION: (4)
<223> OTHER INFORMATION: Xaa is cyclohexylalanine
<220> FEATURE:
<221> NAME/KEY: SITE
<222> LOCATION: (5)
<223> OTHER INFORMATION: Xaa is 4,4-difluoro-2-amino butyric acid
<220> FEATURE:
<223> OTHER INFORMATION: Description of Artificial Sequence: Synthetic
      sequence

<400> SEQUENCE: 12

Glu Xaa Ile Xaa Xaa
  1               5

<210> SEQ ID NO 13
<211> LENGTH: 6
<212> TYPE: PRT
<213> ORGANISM: Artificial Sequence
<220> FEATURE:
<221> NAME/KEY: SITE
<222> LOCATION: (3)
<223> OTHER INFORMATION: Xaa is diphenylalanine
<220> FEATURE:
<221> NAME/KEY: SITE
<222> LOCATION: (5)
<223> OTHER INFORMATION: Xaa is cyclohexylalanine
<220> FEATURE:
<221> NAME/KEY: SITE
<222> LOCATION: (6)
<223> OTHER INFORMATION: Xaa is 4,4,4-trifluoro-2-amino- butyric acid
<220> FEATURE:
<223> OTHER INFORMATION: Description of Artificial Sequence: Synthetic
      sequence

<400> SEQUENCE: 13

Asp Glu Xaa Glu Xaa Xaa
  1               5
```

PEPTIDE INHIBITORS OF HEPATITIS C VIRUS NS3 PROTEASE

TECHNICAL FIELD

This invention relates to compounds which can act as inhibitors of the hepatitis C virus (HCV) NS3 protease, to uses of such compounds and to their preparation.

BACKGROUND ART

The hepatitis C virus (HCV) is the major causative agent of parenterally-transmitted and sporadic non-A, non-B hepatitis (NANB-H). Some 1% of the human population of the planet is believed to be affected. Infection by the virus can result in chronic hepatitis and cirrhosis of the liver, and may lead to hepatocellular carcinoma. Currently no vaccine nor established therapy exists, although partial success has been achieved in a minority of cases by treatment with recombinant interferon-α, either alone or in combination with ribavirin. There is therefore a pressing need for new and broadly-effective therapeutics.

Several virally-encoded enzymes are putative targets for therapeutic intervention, including a metalloprotease (NS2-3), a serine protease (NS3), a helicase (NS3), and an RNA-dependent RNA polymerase (NS5B). The NS3 protease is located in the N-terminal domain of the NS3 protein, and is considered a prime drug target since it is responsible for an intramolecular cleavage at the NS3/4A site and for downstream intermolecular processing at the NS4A/4B, NS4B/5A and NS5A/5B junctions.

Previous research has identified classes of peptides, in particular hexapeptides, showing degrees of activity in inhibiting the NS3 protease. The aim of the present invention is to provide further compounds which exhibit similar, and if possible improved, activity.

DISCLOSURE OF INVENTION

The present inventors investigated the replacement of cysteine by 4,4-difluoro-2-aminobutyric acid or 4,4,4-trifluoro-2-aminobutyric acid at the P1 position of certain peptidic product inhibitors and substrates of HCV NS3 serine protease. These studies have shown that fluorocarbon groups, in particular the —CF$_2$H group may mimic the cysteine thiol group, which is believed to be involved in substrate and inhibitor binding to the S1 specificity pocket of the NS3 protease. In general terms, therefore, the present invention relates to compounds containing fluorocarbon groups, especially —CF$_2$H and —CF$_3$, for use as inhibitors of HCV NS3 protease. Examples of such compounds include peptides or peptide analogs, in which a fluorocarbon group, such as —CF$_2$H, is present as a sidechain, for instance at the C-terminus or P1 position of the peptide.

Definitions

In the discussion of the invention which follows certain terms are used repeatedly. Therefore, we seek to define each at the outset. Where definitions in the text differ from those given here it should be understood that the possibilities set out are those which are preferred among the broader definitions set out here.

By "lower alkyl" and "lower alkoxy" are intended groups having from 1 to 10, preferably 1 to 6, most preferably 1 to 4 carbon atoms. "Lower alkenyl" groups have from 2 to 10, preferably 2 to 6 carbon atoms.

The term "aryl" as used herein is intended to encompass heteroaromatic groups and implies an aromatic (heteroaromatic) ring optionally fused, e.g. benzofused, with one to three cycloalkyl, aromatic, heterocyclic or heteroaromatic rings. Preferred groups containing a carbocyclic aromatic radical have from 6 to 14 more preferably 6 to 10 carbon atoms. Examples of such groups include phenyl and naphthyl. Heteroaryl groups include a 3 to 7 membered heterocyclic aromatic ring consisting of one or more carbon atoms and from one to four heteroatoms selected from nitrogen, oxygen and sulphur. Aryl groups, in general, contain from 1 to 14 carbon atoms, preferably 3 to 10 carbon atoms.

Aralkyl and aralkyloxy-groups generally contain from 2 to 20, preferably 4 to 15 carbon atoms.

Optional substituents may be selected from the following list: lower alkyl or alkenyl, aryl, lower alkoxy, amino, nitro, halo, hydroxy, carboxylic acid, acyl, formyl, acylsulphonamide, ester, amide, cyano, and trihalomethyl groups. As appropriate an optional substituent may itself be substituted by another substituent.

Where a group is described as "optionally interrupted" it may contain at lest one of the following:

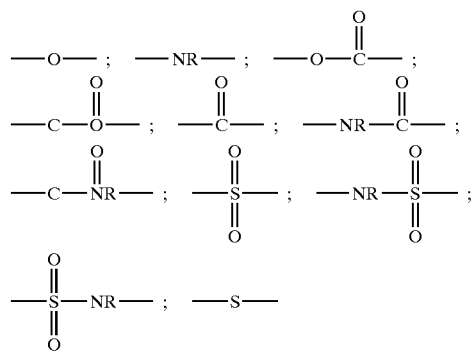

where R is hydrogen, or an alkyl, e.g. lower alkyl, alkenyl, e.g. lower alkenyl, aryl or aralkyl group.

MODES FOR CARRYING OUT THE INVENTION

According to a first aspect of the invention there is provided a peptide of formula (I):

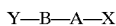

as well as pharmaceutically acceptable salts and esters thereof.

The Group A

In this formula A is an amino acid residue of formula:

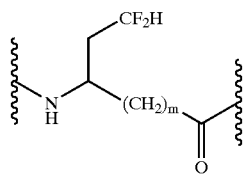

where m is 0 or 1. Preferably, m is 0.

The Group B

B is also a naturally or non-naturally occurring amino acid residue of formula:

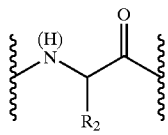

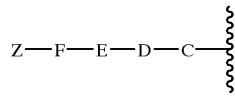

wherein R₂ is a non-polar side chain or includes an acidic functionality. Essentially hydrophobic, polar but uncharged side chains may also be suitable. Typical $R_2$ groups contain from 1 to 20, preferably from 1 to 13 and particularly preferably between 1 and 8 carbon atoms. The side chain, $R_2$, may be aliphatic or aromatic, saturated or unsaturated, branched or unbranched, substituted or unsubstituted. The side chain may contain, in addition to carbon and hydrogen, heteroatoms such as nitrogen, oxygen, sulphur and phosphorus. Preferred substituent groups include the halogens, especially fluorine. In general, the "acidic functionality" is a carboxylic acid group, but the term as used herein encompasses acid mimetics such as tetrazoles and acylsulphonamides. Examples of suitable side chains, $R_2$ include those of glutamic acid and aspartic acid, 2-aminobutyric acid, 4,4-difluoro-2-aminobutyric acid, alanine, isoleucine, valine, leucine, cysteine, phenylalanine, naphthylalanine and β-cyclohexylalanine. Of these, the side chains of cyclohexylalanine and leucine are particularly preferred. The "side chain" present in proline may also be suitable in which case the group $R_2$ forms a ring with the adjacent nitrogen, and the hydrogen placed in parenthesis in the above formula is absent.

The Group X

X is selected from the following:

—$CO_2R_8$; —H; —$OR_8$; —$CF_3$; —$CONR_9R_{10}$; —$CF_2CONR_9R_{10}$; —$NHSO_2R_{25}$ or a heterocyclic group of formula:

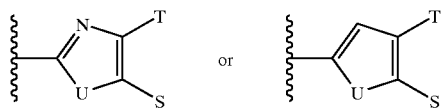

wherein U is sulphur, oxygen or $NR_{11}$; $R_8$, $R_9$, $R_{10}$ and $R_{11}$ are, independently, hydrogen or any suitable aliphatic or aromatic groups such as, in particular, lower alkyl, lower alkenyl, aryl, or aralkyl groups, and S and T are each independently either H or $R_{12}$, where $R_{12}$ is a lower alkyl, lower alkenyl, aryl or aralkyl group, or can together form a ring, such as a 5 or 6 membered ring, preferably an aromatic ring such as a phenyl ring.

$R_9$ is preferably hydrogen, $R_{11}$ is preferably hydrogen, and preferred examples of $R_{10}$ include benzyl and phenethyl.

Preferred choices for the group X are: —$CO_2H$ and —$CONHCH_2Ph$,

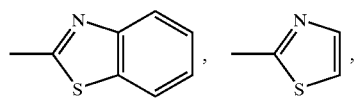

H, —OH, or —$NHSO_2R_{25}$.

The Group Y (i) The N-terminal group, designated Y, may be a group of formula:

wherein, C is a naturally or non-naturally occurring amino acid residue having a non-polar, polar but uncharged, or acidic side chain. Generally, side chains within the definition $R_2$ above are also suitable as side chains at C and examples of amino acids given above for B apply also to C. In this case isoleucine and glutamic acid are particularly preferred, though others such as those discussed below under the heading "tripeptides" may also be used to advantage.

D may be absent (in which case E and F will also be absent), but where present is a naturally or non-naturally occurring amino acid having a hydrophobic side group. This side group may include from 1 to 20, and preferably 1 to 13 carbon atoms. Provided that the essentially hydrophobic character of the side group is retained it may be aliphatic or aromatic, saturated or unsaturated, branched or unbranched, substituted or unsubstituted. The side chain may contain, in addition to carbon and hydrogen, heteroatoms such as nitrogen, oxygen, sulphur and phosphorus. Preferred substituent groups include the halogens, especially fluorine. Examples of suitable residues include methionine, isoleucine, leucine, norleucine, valine, methyl valine, phenylglycine, phenylalanine or diphenylalanine. Among these leucine and, particularly, diphenylalanine are preferred.

E (together with F) may be absent, but if present is generally a naturally or non-naturally occurring amino acid having a side chain which includes an acidic functionality. Preferred examples are glutamic and aspartic acid, with the former being particularly preferred. E may, alternatively, be a naturally or non-naturally occurring amino acid having a non-polar, or polar but uncharged side chain. Of the non-polar amino acids, phenylalanine, diphenylalanine, isoleucine and valine are preferred, especially the D-enantiomers. Among the polar amino acids suitable examples are tyrosine and 4-nitrophenylalanine. Alternatively where F, but not E, is absent (see below), E may be a dicarboxylic acid containing up to 10 carbon atoms preferably up to 6 carbon atoms and lacking the amino group of acidic amino acids. Suitable examples are glutaric and succinic acid.

F may be absent (either by itself, or together with E), but when present is an amino acid or analogue having a side chain including acidic functionality. Aspartic acid is preferred, although glutamic acid is another possibility. Like E, F may also be a dicarboxylic acid containing up to 10, preferably up to 6 carbon atoms, and lacking the amino group of acidic amino acids. Examples are glutaric and succinic acid.

In general, the side chains at E and F may include from 1 to 20, preferably 1 to 13, and particularly preferably 1 to a carbon atoms. They may be aliphatic or aromatic, saturated or unsaturated, branched or unbranched, substituted or unsubstituted. The side chain may contain, in addition to carbon and hydrogen, heteroatoms such as nitrogen, oxygen, sulphur and phosphorus. Preferred substituent groups include the halogens, especially fluorine.

Z may be absent (especially in the case where the N terminus of Y is an E or F group and this is a dicarboxylic acid lacking an amino group). Where present, however, it may be a hydrogen atom or a group of formula $R_7CO$—, where $R_7$ is chosen such that the group $R_7CO$, together with the nitrogen atom to which the group is bonded forms an amide, urethane or urea linkage. $R_7$ contains from 1 to 20 carbon atoms, preferably 1 to 15, particularly 4 to 9 carbon atoms and is an alkyl, aryl or aralkyl group, alkyloxy, aryloxy or aralkyloxy group, alkylamino, arylamino or aralkylamino group. In general, $R_7$ is a relatively small hydrophobic group but it may be substituted for instance with one or more trifluoromethyl substituents or with carboxylic acid groups which may, optionally be esterified, e.g. with a $C_{1-4}$ alkyl group. Preferred examples of $R_7$ include: $ArCH_2O-$ and $ArCH_2NH-$, in which Ar is an optionally substituted aryl (preferably phenyl) group. Preferred optional substituents include the halogens, carboxylic acid, carboxylic acid esters and $-CF_3$ groups. Alternatively, preferred $R_7$ groups include lower alkyloxy groups, especially tBuO-. These groups are particularly preferred in the case of molecules containing just three amino acid residues. In the case of molecules containing four or more residues simple $R_7$ groups such as lower alkyl, especially methyl may be preferable.

(ii) Alternatively, instead of being an amino acid or oligopeptide of formula Z—F—E—D—C—, the N-terminal group Y may be a group of formula $R_{13}CO-$ where $R_{13}$ is an aliphatic or aromatic group containing from 1 to 25, preferably 4–21, particularly 4 to 16 carbon atoms and 0–5 oxygen atoms, 0–3 nitrogen atoms, a to 2 sulphur atoms and up to 9 other heteroatoms (especially halogen atoms) which may be the same or different. Preferred groups, $R_{13}$, contain an acidic functionality (especially a carboxylic acid or acylsulphonamide group) or an indoline group.

Substituent groups, $R_{13}$, which contain an acidic functionality, such as $-CO_2H$ preferably also include a relatively hydrophobic group such as $C_{3\ to\ 8}$ alkylene (which may be branched), cyclopentyl, cyclohexyl, or aryl, especially optionally substituted phenyl or thienyl groups. Optional substituents include halogens, $C_{1-8}$ alkyl and alkoxy groups and $-CF_3$ groups.

Some examples of $R_{13}$ groups including a carboxylic acid group may be represented by the general formula:

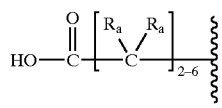

wherein each $R_a$ is independently selected from hydrogen, lower alkyl (especially methyl), lower alkenyl, lower alkoxy, optionally substituted aryl or aralkyl groups (such as those substituted with halogen, $-CF_3$ or lower alkyl or alkoxy groups) or two $R_a$ taken together result in the formation of a three to seven membered aliphatic or aromatic ring which optionally contains at least one heteroatom. In the case where two $R_a$ taken together result in the formation of a ring containing unsaturation, especially an aromatic ring, then other $R_a$ may be absent. Optionally one or more groups

may be replaced by $-O-$. Preferably no more than one such group is replaced.

A preferred subclass of these compounds are those of formula

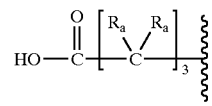

especially those compounds in which each $R_a$ is independently selected from hydrogen, methyl, optionally substituted phenyl or two $R_a$ on the same carbon atom together form a cyclopentyl, cyclohexyl, or a five or six membered cyclic ketal. Examples of such compounds are those of formulae 7d, 7e, 7f, 7j, 7k, 7l, 7o, 7p and 7q in Table 3 infra.

Another preferred subclass is

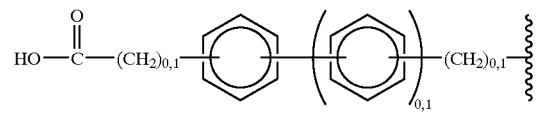

such as compounds 8b, 8c, 8d, 8e and 8g in Table 3.

The carboxylic acid group in any of this preferred class of compounds may be esterified for instance as a lower alkyl ester such as a methyl ester.

The $-OH$ group of the carboxylic acid group may also optionally be replaced by an $-SO_2NH-$ group, especially by $Ph-SO_2-NH-$ (e.g. compound 7n of Table 3). Other preferred substituent groups $R_{13}$ have the formula

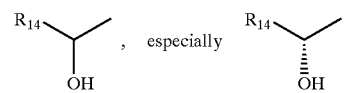

where $R_{14}$ is a cycloalkyl ($C_{3-7}$, but especially cyclohexyl) or optionally substituted aryl group. Optional substituents include $C_{1-8}$ alkoxy, halogen or $-CF_3$ but preferably $R_{14}$ is an unsubstituted cyclohexyl, phenyl or thienyl group.

Another possibility is that $R_{13}$ is an indoline group of formula

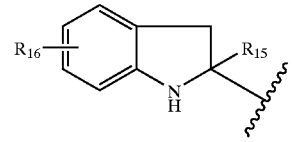

where $R_{15}$ is hydrogen, an optionally branched, optionally interrupted and optionally substituted lower alkyl or lower alkenyl group or an optionally substituted aralkyl group $R_{16}$ is hydrogen or an optionally substituted and optionally interrupted lower alkoxy or aryloxy-group.

Preferred optional interruptions in the group $R_{15}$ include $-O-$. A preferred substituent is $-CO_2H$, optionally as a lower alkyl ester. When $R_{15}$ is an aralkyl group it is preferably an optionally substituted benzyl- or thienylmethyl-group. Preferred optional substituents in the benzene ring include halogens, especially chlorine, lower alkoxy (e.g. $-OMe$) and aryloxy (e.g. $PhO-$) groups cyano-, and carboxylic acid groups. Carboxylic acid groups, optionally in the form of lower alkyl esters are especially preferred. The preferred position of substitution depends on the particular aryl group substituted, and the nature of the substituent. In the case where $R_{15}$ is a benzyl group, substitution is preferably ortho-, or meta- to the $-CH_2-$ group.

The substituent $R_{16}$, when present is preferably at the 6-position of the ring system. Optional substituents of $R_{16}$ include carboxylic acid groups, possibly as lower alkyl esters. Possible interrupting groups include: —O—, —SO$_2$—, —CO—, —OCO—, —CO.O—, —NH—, —NH.CO—, and —CO.NH—. Of these —O— and —SO$_2$— are preferred.

In another embodiment $R_{13}$ is a group of formula:

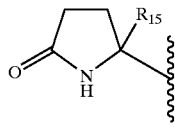

where $R_{15}$ is as defined above.

In a still further embodiment it is an optionally substituted indole group of formula:

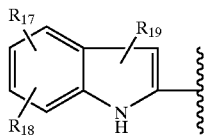

where each of $R_{17}$, $R_{18}$ and $R_{19}$, independently, is selected from hydrogen, optionally substituted lower alkyl, lower alkenyl and lower alkoxy, optionally substituted aryl, aralkyl, aryloxy or aralkoxy, a carboxylic acid group optionally as its lower alkyl ester, a halogen, cyano, or CF$_3$ group.

Tables 3 and 4 list, under the column "structure" certain other possibilities for $R_{13}$.

Stereochemistry

Generally, each naturally or non-naturally occurring amino acid, (A—F) may have D- or L-stereochemistry, but L-stereochemistry is generally preferred. However, either D- or L-stereochemistry is allowed at amino acid A, although in general the L isomer is preferred. Particularly preferably, all the naturally or non-naturally occurring amino acid residues in the peptides of this aspect of the invention are L-isomers.

Compounds of this aspect of the invention may be substantially pure single stereoisomers, or may be mixtures of stereoisomers, especially of diastereoisomers having different stereochemistry at the A amino acid only.

The first aspect of the invention includes certain preferred classes of compound as will now be discussed.

(1) "Dipeptides"

Preferred dipeptides of the first aspect of the invention are ketoacids; that is, the group X is preferably a —CO$_2$H group.

The amino acid residue A of preferred dipeptides has m=a. Preferred compounds have leucine, or cyclohexyl alanine as residue B.

Particularly preferred dipeptides are those of formula:

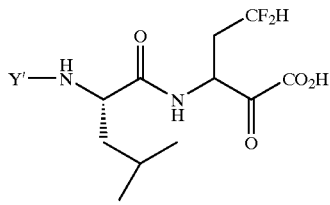

where Y' is a group selected from those discussed at (ii) above. Examples are given in tables 3 and 4.

(2) "Tripeptides"

In preferred tripeptides of the first aspect of the invention, X is preferably —H or —CO$_2$H, of which the latter is particularly preferred. As in the dipeptides, m is preferably 0.

Preferred residues at B are cyclohexylalanine, leucine, α-amino butyric acid, 4,4-difluoro-2-aminobutyric acid and phenylalanine, with leucine being particularly preferred.

Thus, particularly preferred C-terminal portions (—B—A—X) of the tripeptides are represented by the following formulae:

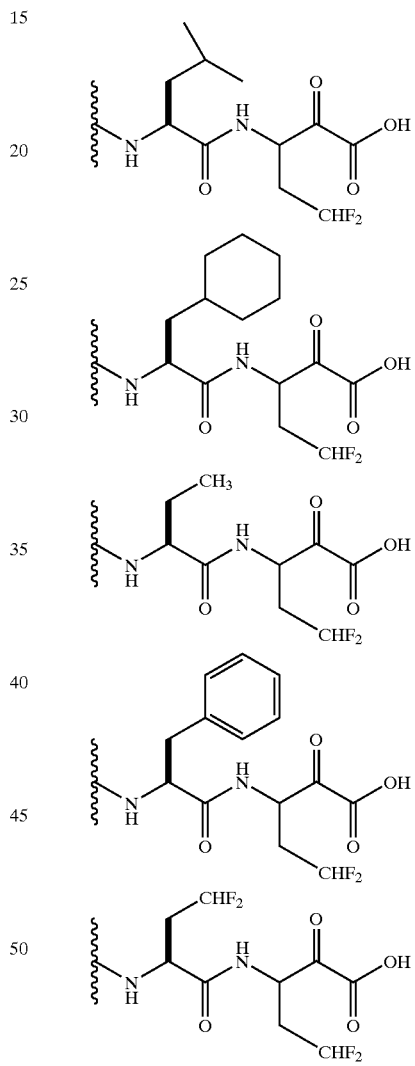

Preferred amino acids for inclusion as amino acid "C" of the tripeptide, for instance in conjunction with one of the particularly preferred C terminal portions set out above include alanine, isoleucine, leucine, phenylalanine, valine, norleucine, norvaline, glutamic acid, glutamine, aspartic acid, α-t-butyl glycine, styrylalanine, homoleucine, 3,5 dichlorophenylalanine 2-thienylalanine, 3-bromophenylalanine and α-cyclopentyl glycine.

Particularly preferred C-terminal portions including these amino acids include the following:

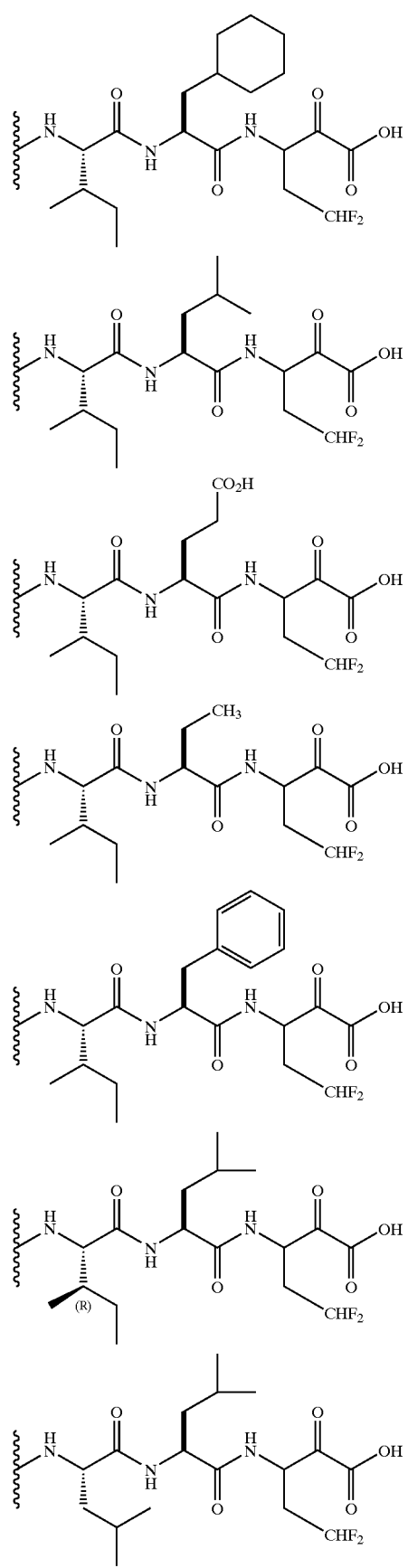
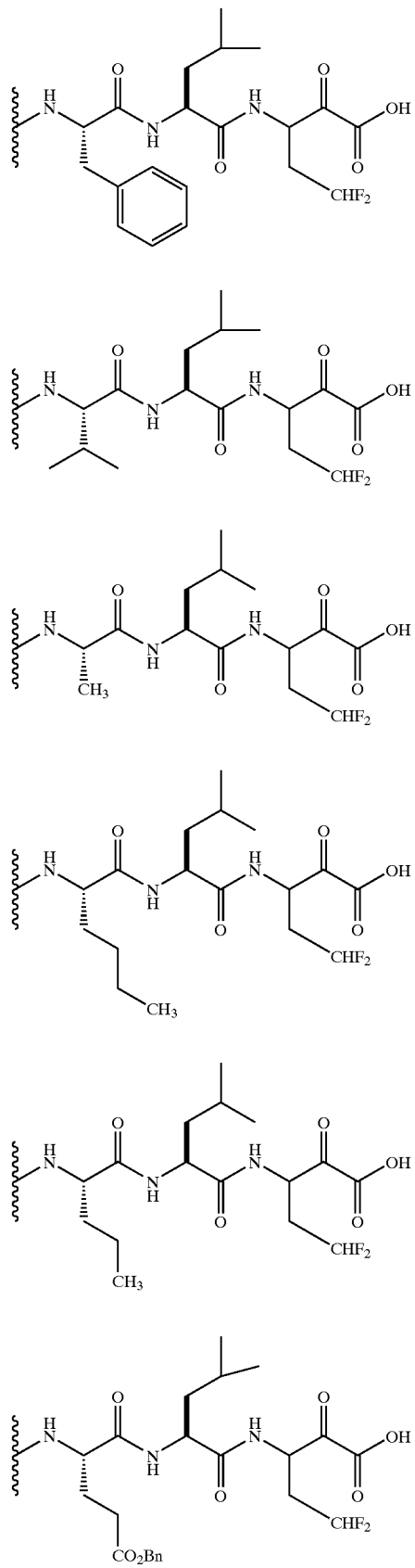

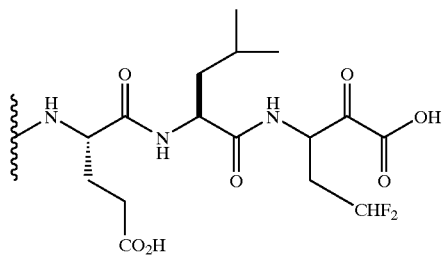
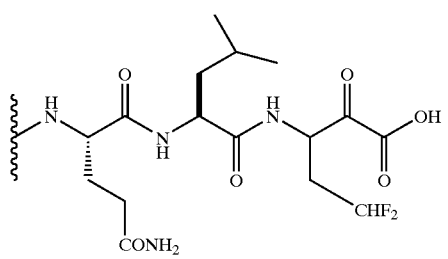
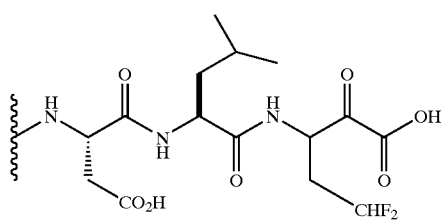
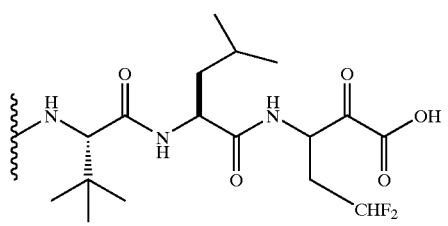
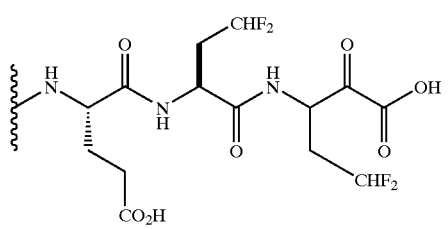
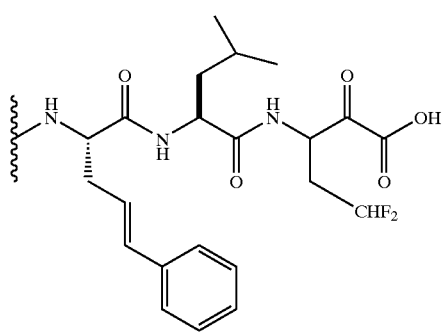
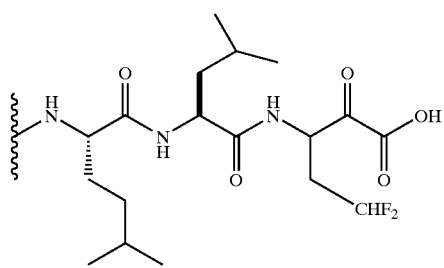
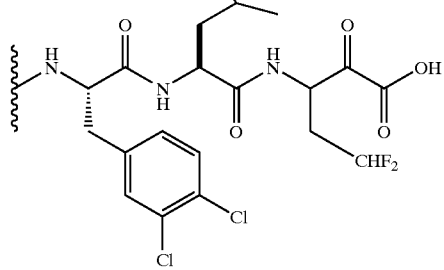
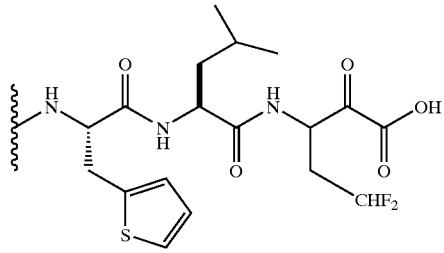
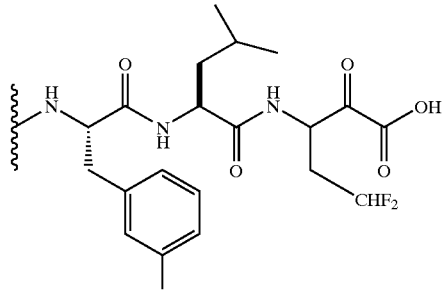
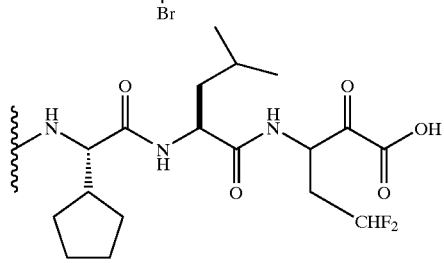
As indicated above, various N-terminal groups are possible and preferably result in the formation of an amide, urethane or urea linkage. The following are among the preferred N-terminal groups for tripeptides:
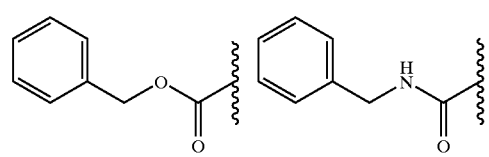

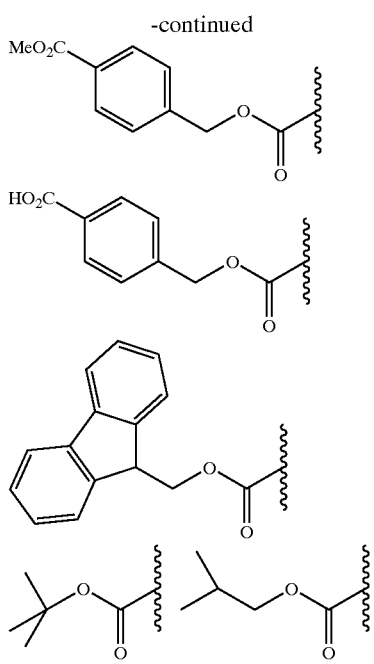

Specific examples of tripeptides in accordance with the first aspect of the invention, together with their IC₅₀s are set out below at Table 2.

(3) Tetrapeptides

Preferred C-terminal "X" groups for inclusion in tetrapeptides of the invention are —CO₂H (optionally in the form of its ester) and —CONR₉R₁₀ where R₉ and R₁₀ are as defined above. As in the other series, "m" is preferably 0.

Any of the tripeptide fragments described above may be extended at the C-terminus by addition of an amino acid within the definition "D" above. Diphenylalanine is particularly preferred.

A particularly preferred tetrapeptide unit: D—C—B—A is:

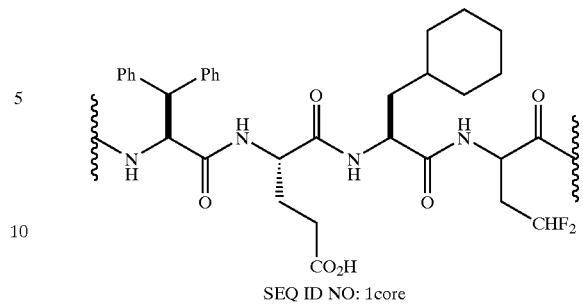

SEQ ID NO: 1core which may be joined at its N- and C-termini to any of the X or Z groups set out above.

Preferred tetrapeptides are set out in Table 2.

(4) Hexapeptides

Hexapeptides in accordance with the first aspect of the invention are compounds of formula:

Z—F—E—D—C—B—A—X where A—F, X and Z are defined above. "m" is preferably 0. Hexapeptides may be based on any of the preferred tripeptides, C—B—A, set out above, extended at their C-termini by amino acids within the definitions D, E and F. A wide variety of X groups is possible, but —OH, acylsulphonamide, —H and —CO₂H are preferred. Relatively small Z groups are preferred. In particular, Z together with its adjacent NH group may form a lower alkyl amide group.

Preferred hexapeptides

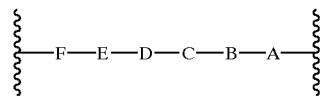

include:

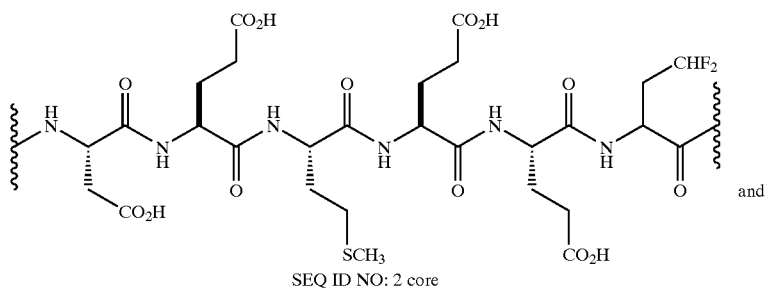

SEQ ID NO: 2 core

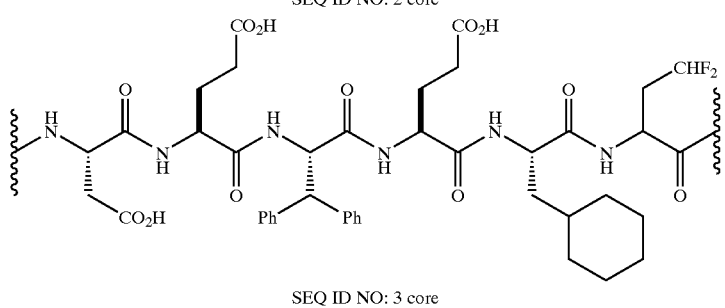

SEQ ID NO: 3 core

Examples of hexapeptides of the first aspect of the invention can be found at Table 1.

In a second aspect, the invention is particularly concerned with molecules of formula:

Y—B—A'—X'    (FORMULA II)

where the groups Y and B are as defined above and X' is —OH, or —NHSO$_2$R$_{25}$, where R$_{25}$ is as defined above, and pharmaceutically acceptable salts and esters thereof.

A' is a naturally, or non-naturally occurring amino acid residue of formula

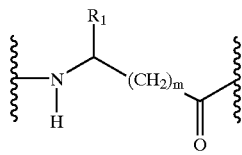

wherein m is 0, or 1 (preferably 0) and R$_1$ is a fluorine-substituted hydrocarbyl side chain. The hydrocarbyl side chain may be an alkyl, alkenyl, aralkyl, or aryl group having from 1 to 15, preferably 2 to 10, particularly 2 to 8 carbon atoms. The side chain preferably includes at least one, more preferably at least two, fluorine atoms at the position γ- to the carbonyl group of the amino acid including the fluorinated side chain.

Examples of suitable side chains are:

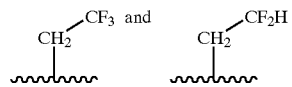

Of these,

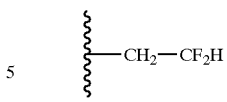

is particularly preferred.

As with the compounds of the first aspect of the invention each naturally or non-naturally occurring amino acid, (A—F) may have D- or L-stereochemistry, but L-stereochemistry is generally preferred. However, either D- or L-stereochemistry is allowed at amino acid A, although in general the L isomer is preferred. Particularly preferably all the naturally or non-naturally occurring amino acid residues in the peptides of this aspect of the invention are L-isomers.

Compounds of this aspect of the invention may be substantially pure single stereoisomers, or may be mixtures of stereoisomers, especially of diastereoisomers having different stereochemistry at the A amino acid only.

Particularly preferred molecules of this aspect of the invention are hexapeptides. For example, the following formulae show preferred hexapeptides of the second aspect of the invention:

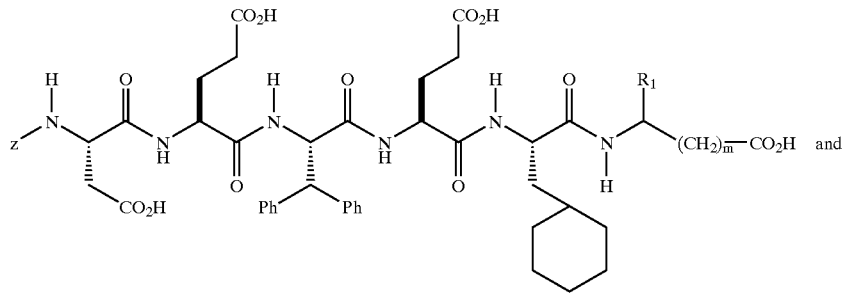

SEQ ID NO: 4 core

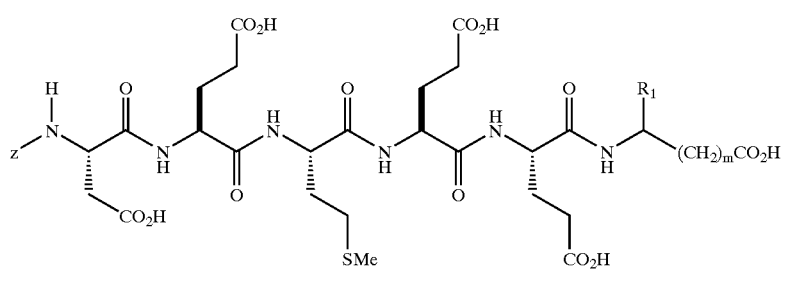

SEQ ID NO: 5 core where Z is as defined above for the first aspect, and is preferably an acyl group, for example an acetyl group and R$_1$ is a fluorinated hydrocarbon side chain having from 1 to 15, preferably 2 to 10, particularly 2 to 8 carbon atoms.

Examples of hexapeptides of the second aspect of the invention are included in Table 1 (see compounds 1a, 1b, 1g, and 1 h).

Compounds of the first and second aspects of the invention typically inhibit the action of HCV NS3 protease at concentrations (IC$_{50}$s) of 100 μM and below. The longer peptides are generally inhibitory at lower concentrations than the shorter ones because of their greater potential for enzyme binding. However, the activities of the shorter peptides are surprisingly high.

Examples of the hexapeptides of the invention are typically inhibitory at concentrations of 10 μM or below. Some are inhibitory at concentrations of 5 μM or below, or even at 1 μM or below.

Examples of the tripeptides and tetrapeptides of the invention are typically inhibitory at concentrations of 20 μM or below, preferably 10 μM or below, particularly 5 μM or below. Optimised tripeptides may be effective at concentrations below 1 μM.

Examples of the dipeptides of the invention are effective at concentrations of 50 μM or less, preferably 30 μM or less, especially 10 μM or less.

Embodiments of the first and second aspect can therefore be expected to be of use in the treatment and prevention of hepatitis C and other related conditions.

According to a third aspect of the invention there are provided derivatives of the compounds of the first or second aspect of the invention.

In particular, derivatives include "prodrug" forms of the compounds of Formula I or Formula II which may be converted in vivo into the compound of Formula I or II. Examples of such derivatives include those in which one or more carboxylic acid groups of the compound of Formula I or II are esterified or otherwise derivatised into groups convertible in vivo into carboxylic acid or carboxylate groups. For instance carboxylic acid groups may be esterified with $C_1$–$C_{18}$ alcohols, preferably $C_1$–$C_8$ alcohols. Another possibility is that the derivative may be a C-terminal extended variant of the compound of Formula I or II, convertible in vivo into a compound of Formula I or II.

According to a fourth aspect the present invention provides a compound or derivative according to the first, second or third aspect, for use in any therapeutic method, preferably for use in inhibiting the HCV NS3 protease, and/or for use in treating or preventing hepatitis C or a related condition. By "related condition" is meant a condition which is or can be caused, directly or indirectly, by the hepatitis C virus, or with which the HCV is in any way associated.

According to a fifth aspect the present invention provides the use of a compound or derivative according to the first, second or third aspect in the manufacture of a medicament for the treatment or prevention of hepatitis C or a related condition.

A sixth aspect of the invention provides a pharmaceutical composition which includes one or more compounds or derivatives according to the first, second, or third aspect.

The composition may also include pharmaceutically acceptable adjuvants such as carriers, buffers, stabilisers and other excipients. It may additionally include other therapeutically active agents, in particular those of use in treating or preventing hepatitis C or related conditions.

The pharmaceutical composition may be in any suitable form, depending on the intended method of administration. It may for example be in the form of a tablet, capsule or liquid for oral administration, or of a solution or suspension for administration parenterally.

According to a seventh aspect of the invention, there is provided a method of inhibiting HCV NS3 protease activity, and/or of treating or preventing hepatitis C or a related condition, the method involving administering to a human or animal (preferably mammalian) subject, e.g. one suffering from the condition, a therapeutically or prophylactically effective amount of a composition according to the sixth aspect of the invention, or of a compound or derivative according to the first aspect. "Effective amount" means an amount sufficient to cause a benefit to the subject or at least to cause a change in the subject's condition.

The dosage rate at which the compound, derivative or composition is administered will depend on the nature of the subject, the nature and severity of the condition, the administration method used, etc. Appropriate values can be selected by the trained medical practitioner. Preferred daily doses of the compounds are likely to be of the order of about 1 to 100 mg. The compound, derivative or composition may be administered alone or in combination with other treatments, either simultaneously or sequentially. It may be administered by any suitable route, including orally, intravenously, cutaneously, subcutaneously, etc. Intravenous administration is preferred. It may be administered directly to a suitable site or in a manner in which it targets a particular site, such as a certain type of cell—suitable targeting methods are already known.

An eighth aspect of the invention provides a method of preparation of a pharmaceutical composition, involving admixing one or more compounds or derivatives according to the first, second or third aspect of the invention with one or more pharmaceutically acceptable adjuvants, and/or with one or more other therapeutically or prophylactically active agents.

The compounds themselves may be prepared by reacting a compound of formula Y—NH—$CHR_2$—$CO_2H$, optionally in a protected form, with an appropriate amine co-reactant (depending on the intended nature of $R_1$ and X in the final compound), examples of which include:

FORMULA K

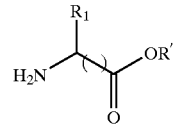

(for X=OH, as in compounds 1a, 1b, 1 g and 1 h in Table 1 infra), R' being a protecting group;

FORMULA L

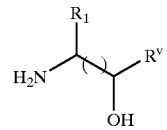

(for X=H, or a functional group other than OH eg, as in compounds 1c, 1d, 1e, 1f, 1i 1j, 1k, 1l, 1m, 1n or 1o in Table 1 infra), $R^v$ corresponding to, or being convertible into the functional group, X; and

FORMULA M

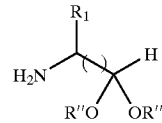

(for X=H, as in compound 1c, R" being a lower alkyl group such as methyl or ethyl).

Compounds of formula I or II having m=1 may be produced using homologs of the above compounds of formulae K, L and M including an additional $CH_2$ group at the appropriate position which is indicated by brackets in the formulae, and also in formula. N below. However, since elongating the chain in P1 may lead to significant loss of activity it is preferred that m=O.

Compounds of formulae K, L and M may be used as racemates or, alternatively, as individual D- or L-isomers. When a racemate is used subsequent separation of product diastereomers may be desirable.

In each case, the reaction can be carried out using standard methods of peptide synthesis. In the case of formula L, oxidation of the hydroxyl to a carbonyl group is also needed. In all cases, protecting groups may need to be removed, for instance under mildly acidic or basic conditions, to reach the final product.

A preferred compound of formula K is racemic 4,4-difluoro-2-aminobutyric acid. One possible scheme for the preparation of this compound is set out below in scheme 1

Scheme 1ª

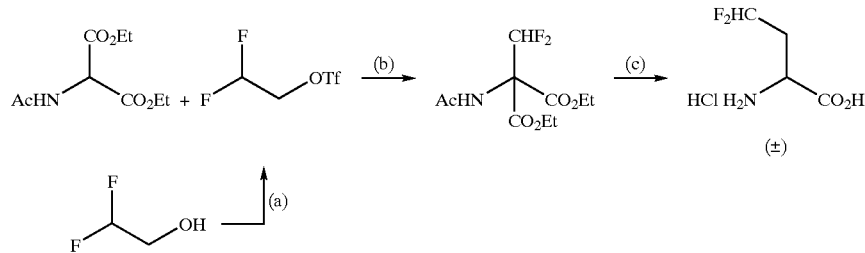

ªReagents: (a) Tf₂O, CH₂Cl₂, Et₃N; (b) KOᵗBu, THF, Δ; (c) 6 N HCl, reflux

The individual R- and S-enantiomers of 4,4-difluoro-2-aminobutyric acid may be prepared from D- and L-aspartic acid, respectively using the method described by Winkler et al in Synthesis (1996), 1419–1421. The carboxylic acid group of these compounds may be protected, for instance by formation of t-butyl esters as shown below in scheme 2

Scheme 2ª

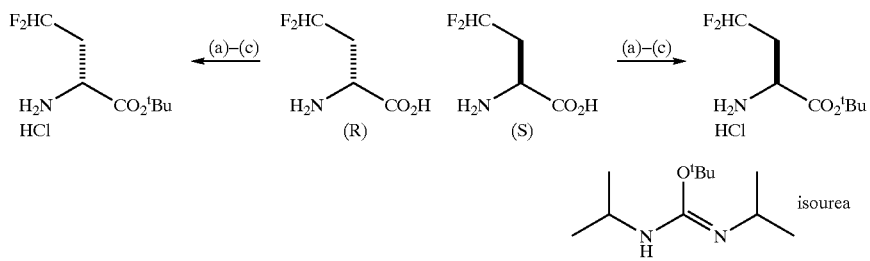

ªReagents: (a) CbzOSu, Na₂CO₃, dioxane; (b) isourea, CH₂Cl₂; (c) H₂, Pd/C, ether/HCl One example of a racemic diacetal of formula M may be prepared as outlined below in scheme 3 which begins with racemic 4,4-difluoro-2-aminobutyric acid.

Scheme 3ª

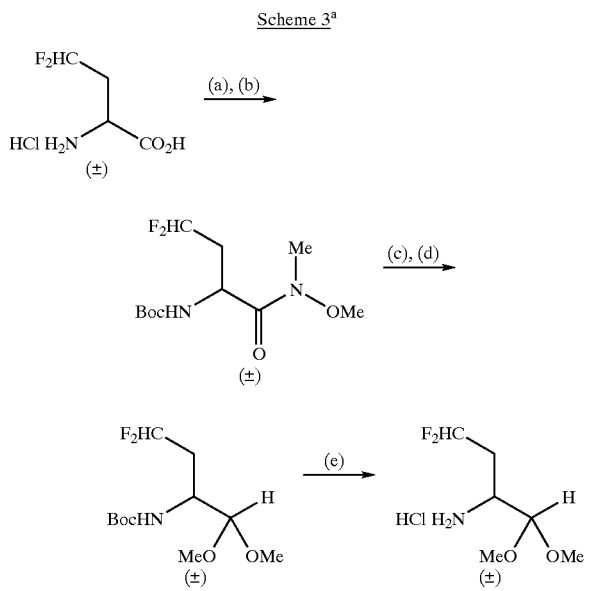

ªReagents: (a) Boc₂O; (b) NH(OMe)Me•HCl, EDC, HOBt, iPr₂NEt; (c) Dibal, THF, -78° C.; (d) HC(OMe)₃, TsOH; (e) HCl (gas), MeOH One example of a compound of formula L, which is particularly suitable for the production of compounds in which X is a ketoacid group is that of formula L' below

FORMULA L'

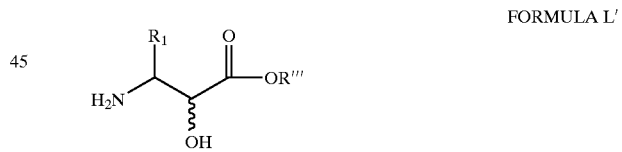

where R''' is a protecting group for carboxylic acids, such as a lower alkyl group. The compound is optionally in the form of its acid addition salt.

A particularly preferred example of such a compound is

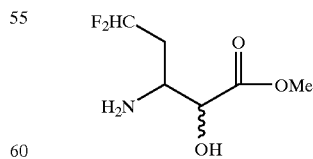

This may be prepared according to the scheme set out below at Scheme 4.

Scheme 5 below shows one example of how this compound may be reacted with a tripeptide to form a tetrapeptide. The same procedure could be employed to make other oligopeptides of the invention.

Scheme 4[a]

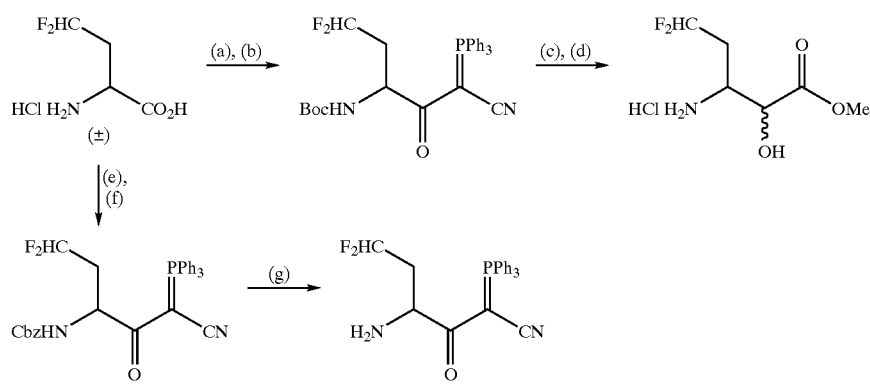

[a]Reagents: (a) Boc₂O; (b) Ph₃P=CHCN, EDC, DMAP; (c) O₃, CH₂Cl₂, MeOH, -78° C.; NaBH₄, MeOH; (d) HCl, EtOAc; (e) CbzOSu, Na₂CO₃, dioxane; (f) Ph₃P=CHCN, EDC, HOBt, CH₂Cl₂; (g) Pd/C, NH₄HCO₂, MeOH

Scheme 5[a]

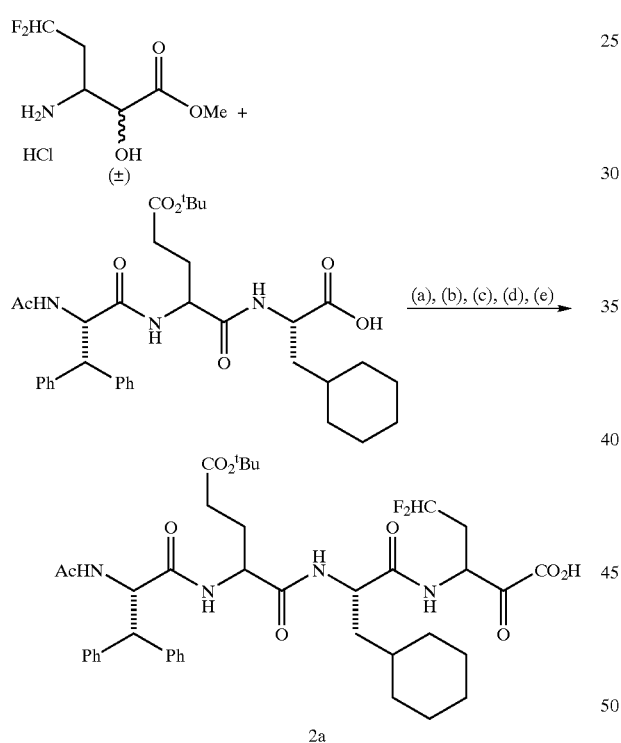

[a]Reagents: (a) HATU, DMF, 2, 6-lutidine; (b) Dess-Martin periodinane, CH₂Cl₂; (c) TFA, CH₂Cl₂ H₂O; (d) 1 N NaOH, MeOH; (e) RP-HPLC An alternative intermediate for the production of compounds having ketoacid functionally at X is a phosphorane based precursor which has the formula shown below:

FORMULA N

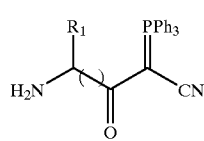

and the production of a preferred example of such a compound:

FORMULA N′

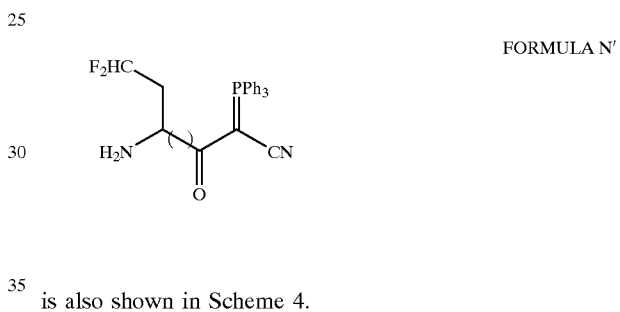

is also shown in Scheme 4.

These compounds may be reacted with optionally protected compounds of formula Y—NH—CHR₂—CO₂H to form certain compounds of the present invention.

The use of the phosphorane based precursor is demonstrated in Scheme 6 with the synthesis of the tripeptide keto acids 3c and 5j and the capped dipeptide keto acid 7l. The same reagents and reaction conditions may be used in the production of other oligopeptides of the invention.

Scheme 6[a]

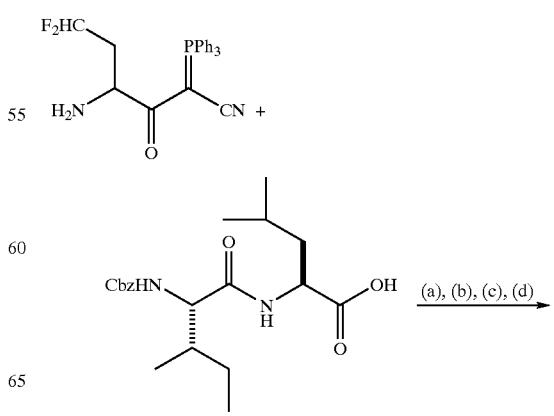

23
-continued
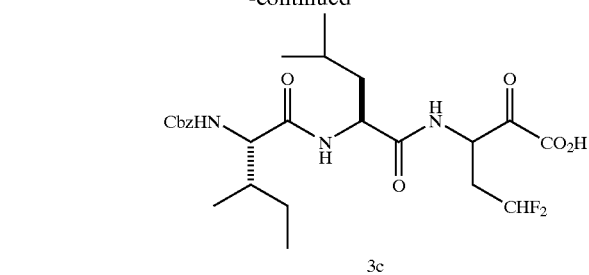
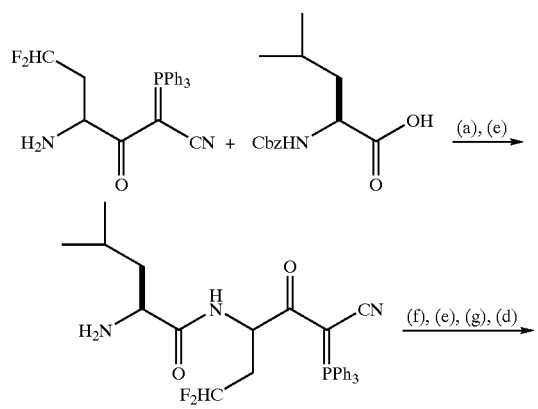
24
-continued
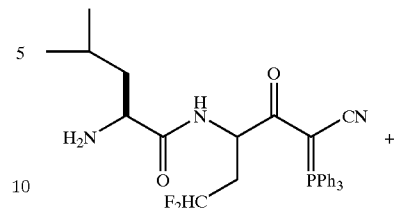
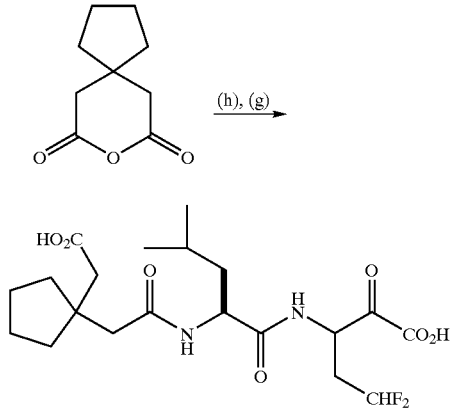
71
[a]Reagents: (a) EDC, HOBt, CH$_2$Cl$_2$; (b) O$_3$, -78° C., CH$_2$Cl$_2$/MeOH; (c) 1 N NaOH, MeOH; (d) RP-HPLC; (e)Pd/C, NH$_4$HCO$_2$; (f) EDC, HOBt, CH$_2$Cl$_2$, BocGlu(OBn)OH; (g) O$_3$, -78° C., CH$_2$Cl$_2$; THF, H$_2$O; (h) CH$_2$Cl$_2$, i-Pr$_2$NEt;
Scheme 7 shows the synthesis of the indoline keto acid inhibitor 9y. Analogous methods may be employed for production of the other indoline keto acids.
Scheme 7[a]
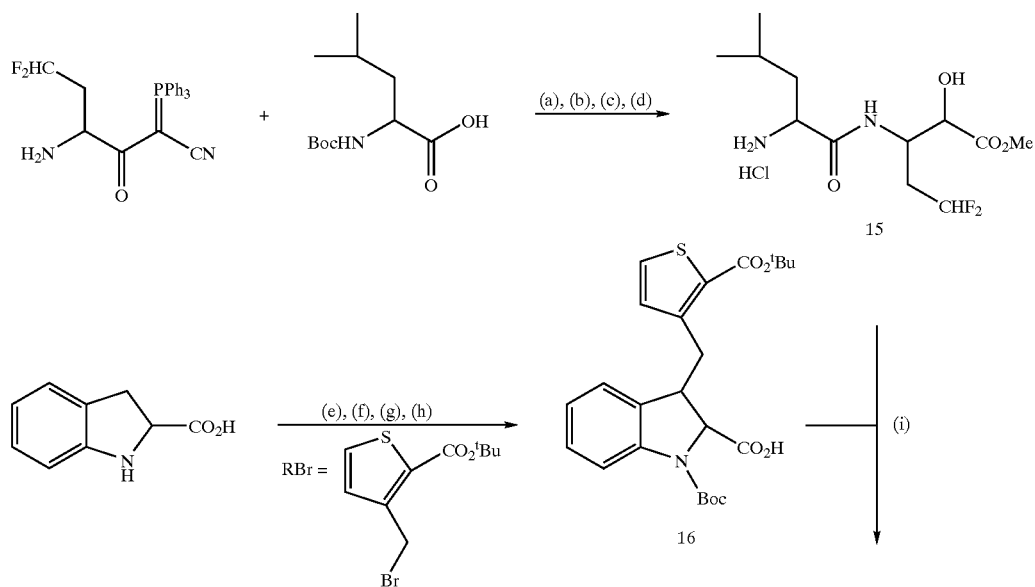

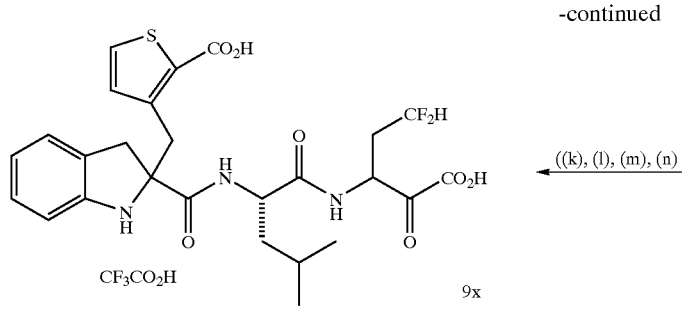

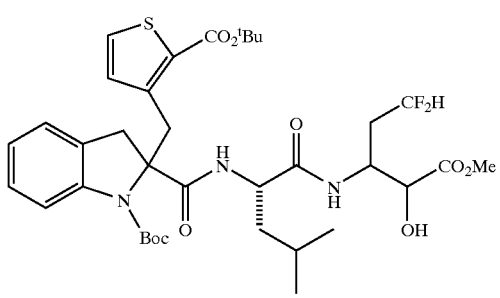

$^a$Reagents: $^a$Reagents: (a) EDC, HOBt, CH$_2$Cl$_2$; (b) O$_3$, -78° C., CH$_2$Cl$_2$/MeOH; (c) NaBH$_4$, MeOH; (d) HCl, dioxane/EtOAc; (e) Boc$_2$O, NEt$_3$, MeOH; (f) BnBr, Cs$_2$CO$_3$, DMF, r.t.; (g) KHMDS, RBr, THF, -78° C. → r.t.; (h) H$_2$, Pd/C, MeOH; (i) HATU, DIPEA, CH$_2$Cl$_2$/DMF (1:1); (k) DMP, CH$_2$Cl$_2$, IBuOH; (l) TFA, CH$_2$Cl$_2$, H$_2$O, TES; (m) 1 N NaOH, MeOH; (n) RP•HPLC.

Compounds of formula Y—NH—CHR$_2$—CO$_2$H may be generated wholly or partly by chemical synthesis, and in particular can be prepared according to known peptide synthesis methods.

Preferably, the compound of formula Y—NH—CHR$_2$—CO$_2$H for reaction with a compound of formula K, L, M or N will be in protected form. For instance, any carboxylic acid groups other than that at the C terminus may preferably be protected, for instance as esters, eg as tertiary butyl esters. Examples of two highly preferred protected pentapeptides suitable for use in synthesis of hexapeptides of the present invention are set out below and labelled (P) and (Q)

(P)

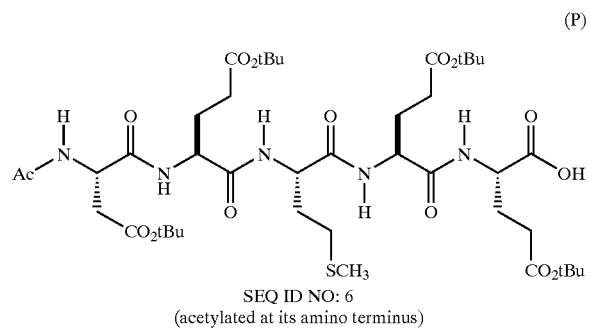

SEQ ID NO: 6
(acetylated at its amino terminus)

(Q)

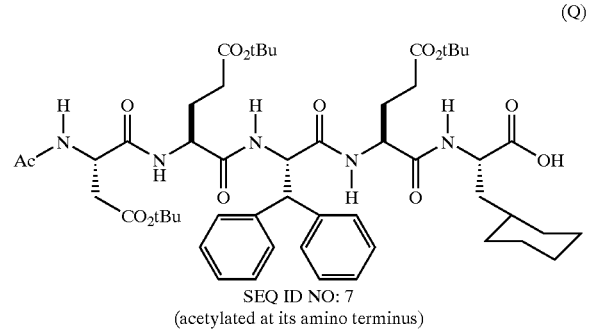

SEQ ID NO: 7
(acetylated at its amino terminus)

The invention provides, according to a ninth aspect, a method as described above for preparing a compound according to the first or second aspect of the invention.

EXAMPLES

Embodiments of the invention are described below by way of example only.

The following abbreviations are used herein:

| | |
|---|---|
| Bn | benzyl |
| CbzOSu | N-(Benzyloxycarbonyloxy)succinimide |
| Dibal | Diisobutylaluminum hydride |
| DIPEA | Diisopropylethyl amine |
| DMAP | 4-Dimethylaminopyridine |
| DMF | Dimethylformamide |
| DMP | Dess Martin periodinane |
| EDC | 1-Ethyl-3-(3'dimethylaminopropyl)carbodiimide hydrochloride |
| HATU | O-(&-Azabenzotriazol-1-yl)-N,N,N'N'-tetramethyluronium hexafluorophosphate |
| HOBt | N-Hydroxybenzotriazole |
| KHMDS | Potassium bis(trimethylsily)amide |
| TES | Triethylsilane |
| Tf$_2$O | Trifluoromethanesulfonic anhydride |
| THF | Tetrahydrofuran |

(1) Synthesis

HPLC Conditions: Reversed phase analytical HPLC was performed on a Waters Symmetry C18 column (150×3.9 mm, 5 μm), flow rate 1 mL/min, using H$_2$O/0.1% TFA (A) and CH$_3$CN/0.1% TFA (B) as eluents; detection at 220 nm with a Waters 996 PDA detector. Gradient 1: linear, 90 A–20% A 8 min, then in 2 min to 0% A, then isocratic. Gradient 2: linear, 70–40% A 10 min. Gradient 3: linear, 90–70% A 10 min. Preparative HPLC was conducted on a Waters Symmetry C18 column (150×19 mm, 7 μm) or a Waters Prep Nova-Pak HR C18 cartridge (40×100 mm, 6 μm) using H$_2$O/0.1% TFA (A) and CH$_3$CN/0.1% TFA (B) as eluents; detection at 220 nm with a Waters 486 absorbance detector.

Example 1

Synthesis of Compound 1a: SEQ ID NO: 5
(Acetylated at its Amino Terminus)

i) (S)-tert-Butyl-2-amino-4,4-difluoro butanoate hydrochloride

Using the procedure described in example 3 (i) for the (R)-enantiomer, the title compound was obtained as an off-white powder; mp 152–153° C. (MeOH, Et$_2$O, pentane); α$_D$+5.1° (c=1.0, anhydrous MeOH). $^1$H-NMR (DMSO-d$_6$) δ 1.44 (s, 9H), 2.36–2.50 (m, 2H), 4.05 (bs, 1H), 6.31 (tt, J=4.5, 55.6 Hz, 1H), 8.71 (bs, 3H); $^{13}$C-NMR (DMSO-d$_6$) δ 27.3, 34.3 (t, J=23.3 Hz), 47.6, 83.5, 114.9 (t, J=238 Hz), 167.1; $^{19}$F-NMR (DMSO-d$_6$) δ −114.4 (d, J=285 Hz), −115.2 (d, J=285 Hz); MS m/z 196 (M$^+$+H).

ii) (1a)

The protected pentapetide shown below (ac-tert-butyl-asp-tert-butyl-glu-met-tert-butyl-glu-tert-butyl-glu) was employed in this example

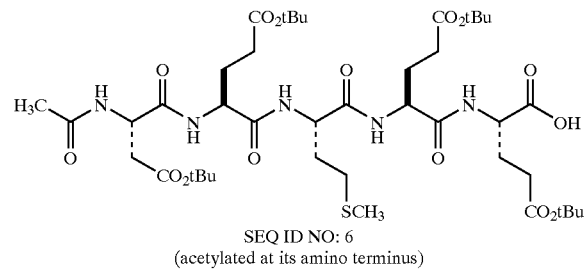

SEQ ID NO: 6
(acetylated at its amino terminus)

30 mg pentapetide (0.03 mmol) was dissolved in dichloromethane (0.5 mL) and cooled to 0° C. N-Ethyl, N'-(dimethylamino)propylcarbodiimide hydrochloride (EDC) (6.3 mg, 0.033 mmol) and hydroxybenzotriazole (HOBT) (4.9 mg, 0.036 mmol) were added, followed by solid (S)-tert-butyl-2-amino-4,4-difluoro-butanoate hydrochloride (from i, above) (10.4 mg, 0.045 mmol) and diisopropylethylamine (0.01 mL, 0.06 mmol). The resulting solution was stirred overnight at room temperature, then taken into ethyl acetate (50 mL) and washed successively with 1 N HCl (2×25 mL), saturated aqueous NaHCO$_3$ (2×20 mL), and brine. Drying (Na$_2$SO$_4$) and evaporation gave a solid which was immediately treated with a solution of trifluoroacetic acid, dichloromethane and water (60/30/10, v/v/v; 10 mL). After 30 min at room temperature the solvents were evaporated in vacuo and the remaining solid separated by preparative HPLC (Waters Symmetry column). Flow 17 mL/min; Gradient: linear, 90% A, 3 min isocratic, in 15 min to 75% A; 7 mg of crude per injection. The product, compound 1a (RT 10.4 min), 12 mg (50%), was obtained as a colourless solid after lyophilization.

$^1$H-NMR (DMSO-d$_6$) δ 1.73–1.95 (m, 8H), 1.83 (s, 3H), 2.02 (s, 3H), 2.19–2.30 (m, 8H), 2.35–2.48 (m, 3H), 2.61 (dd, J=5.2, 11.7 Hz, 1H), 4.14–4.26 (m, 3H), 4.29 (m, 1H), 4.36 (m, 1H), 4.50 (dd, J=5.4, 7.7 Hz, 1H), 6.05 (ddt, J=4.6, 51.6 Hz, 1H), 7.92 (d, 1H, J=8.4 Hz, 1H), 7.96 (d, 1H, J=8.2 Hz, 1H), 7.99 (m, 2H), ), 8.18 (d, 1H, J=7.5 Hz, 1H), 8.33 (bd, 1H, J=7.0 Hz, 1H), 11.9–12.4 (bs, 5H); $^{19}$F-NMR (DMSO-d$_6$) δ –115.0 (d, J=282 Hz), –115.8 (d, J=284 Hz); MS m/z 815 (M$^+$+H)

Example 2

Synthesis of Compound 1b$^1$

In this example, (S)-tert-butyl-2-amino-4,4-difluoro-butanoate hydrochloride (prepared as described in example 1, i)) was used in the preparation of the first diastereomer of compound 1b.

This example, and also examples 3, 4 and 5 below, employed the protected pentapeptide shown below (Ac-tert-butyl-asp-tert-butyl-glu-diphenylala-tert-butyl-glu-cyclohexyl-ala)

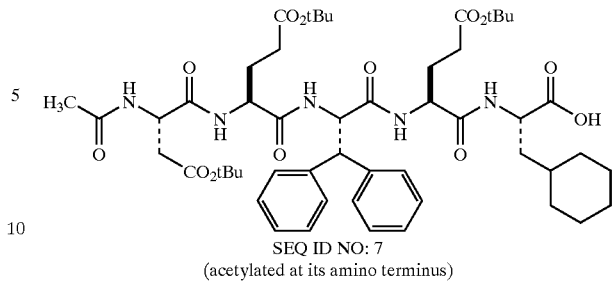

SEQ ID NO: 7
(acetylated at its amino terminus)

i) (1b$^1$)

50 mg pentapetide (0.05 mmol) was dissolved in DMF (0.5 mL) and cooled to 0° C. HATU and solid (S)-tert-butyl-2-amino-4,4-difluoro-butanoate hydrochloride were added, followed by 2,6-lutidine (0.024 mL, 0.2 mmol). The reaction was allowed to reach room temperature and stirred for 3 h. Analytical HPLC (gradient 1) indicated incomplete conversion of the pentapeptide (~30% remaining, RT 10.4 min, gradient 1, product 11.9 min). After another 2 h the mixture was taken into ethyl acetate (100 mL) and washed successively with 1 N HCl, (2×50 mL), saturated aqueous NaHCO$_3$ (2×50 mL), and brine. Drying with sodium sulfate and evaporation gave a light yellow solid which was immediately deprotected with a solution of trifluoroacetic acid, dichloromethane and water (60/30/10, v/v/v; 10 mL). After 30 min at room temperature the solvents were evaporated in vacuo and the remaining solid separated by preparative HPLC (Waters Symmetry column). Flow 17 mL/min; Gradient: linear, 68% A, 3 min isocratic, in 17 min to 65% A; 6 mg of crude per injection. The first peak was deprotected pentapetide (RT 11.6 min), the second the desired product compound 1b (RT 12.2 min); 11 mg (23%) of a colourless solid after lyophilization.

$^1$H-NMR (DMSO-d$_6$) δ 0.76–0.95 (m, 2H), 1.08–1.32 (m, 4H), 1.32–1.41 (m, 1H) 1.42–1.51 (m, 1H), 1.53–1.80 (m, 9H), 1.83 (s, 3H), 1.97–2.35 (m, 6H), 2.38–2.50 (m, 2H), 4.04–4.13 (m, 2H), 4.13–4.21 (m, 1H), 4.27–4.37 (m, 1H), 4.38 (d, J=10.3 Hz, 1H), 4.47 (m, 1H), 5.19 (app. t, J=9.5 Hz, 1H), 6.04 (ddt, J=4.0, 5.7, 56.2 Hz, 1H), 7.05–7.33 (m, 10H), 7.75 (d, 1H. J=7.3 Hz, 1H), 7.79 (d, 1H, J=8.0 Hz, 1H), 7.89 (d, 1H, J=8.1 Hz, 1H), ), 7.96 (d, 1H, J=7.6 Hz, 1H), 8.10 (d, 1H, J=7.0 Hz, 1H), 8.10–8.12 (bs, 1H); MS m/z 929 (M$^+$–H).

Example 3

Synthesis of Compound 1b$^2$ i) (R)-tert.-Butyl-2-amino-4,4-difluoro-butanoate hydrochloride 1.5 g (10.78 mmol) of (R) 2-Amino-4,4-difluoro butanoic acid (prepared as described in Winkler et al, Synthesis 1419, 1996) was dissolved in aqueous half saturated Na$_2$CO$_3$ (50 mL) and cooled to 0° C. A solution of (benzyloxycarbonyloxy)succinimide (2.69 g, 10.78 mmol) in dioxane (50 mL) was added dropwise over 30 min. The resulting suspension was stirred overnight at room temperature. After evaporation of the dioxane under reduced pressure, water (20 mL) and EtOAc (150 mL) were added. The aqueous phase was brought to pH 2 by addition of 1 N HCl, the organic phase was separated, washed with brine and dried. Evaporation gave 2.85 g (97%) of a colourless oil.

This material (950 mg; 3.55 mmol) was dissolved in dichloromethane (15 mL) and N,N'-isopropyl-O-tert-butyl isourea (1.42 g, 7.10 mmol) was added dropwise. The solution was brought to gentle reflux. After 8 h another 1.42 g of the isourea was added and reflux was continued overnight. The diisopropylurea was removed by filtration, and the residue purified by flash chromatography (petroleum ether/ethyl acetate 10:1) to give a colourless oil (844 mg; 72%). $^1$H-NMR (DMSO-$d_6$) δ 1.38 (s, 9H), 2.14–2.28 (m, 2H), 4.08 (m, 1H), 5.03 (d, J=12.6 Hz, 1H), ), 5.06 (d, J=12.6 Hz, 1H), 6.10 (tt, J=4.7, 56.2 Hz, 1H), 7.27–7.39 (m, 5H), 7.79 (d, J=8.1 Hz, 1H); $^{13}$C-NMR (DMSO-$d_6$) δ 27.4, 34.9 (t, J=22.5 Hz), 49.5, 65.5, 81.2, 115.9 (t, J=238 Hz), 127.7, 127.8, 128.3, 136.7, 135.8, 169.8; $^{19}$F-NMR (DMSO-$d_6$) δ −115.1 (d, J=283 Hz), −115.8 (d, J=283 Hz); MS m/z 330 ($M^+$: +H).

300 mg (0.91 mmol) of this material were hydrogenated over 10% palladium-on-charcoal in methanol (10 mL). After 5 h, the catalyst was removed by filtration, then some ethyl acetate and a 1 N solution of hydrochloric acid in diethyl ether (1.37 mL) were added. After evaporation in vacuo the title compound (203 mg; 96%) was obtained as an off-white solid; mp 153–154° C.; $^1$H-NMR (DMSO) δ 1.44 (s, 9H), 2.38–2.50 (m, 2H), 4.03 (t, J=6.2 Hz, 1H), 6.35 (tt, J=4.3, 55.6 Hz, 1H), 8.85 (bs, 3H); $^{13}$C-NMR (DMSO-$d_6$) δ 27.3, 34.3 (t, J=23.3 Hz), 47.6, 83.4, 114.9 (t, J=238 Hz), 167.0; $^{19}$F-NMR (DMSO-$d_6$) δ −114.5 (d, J=285 Hz), −115.3 (d, J=285 Hz); MS m/z 196 ($M^+$+H).

ii) (1b$^2$)

The method for the coupling is described in example 2, i).

After 3 h analytical HPLC indicated only minor amounts of the protected pentapeptide. After workup the crude product was deprotected as described in example 2 and separated by preparative HPLC (Waters Symmetry column). Flow 17 mL/min; Gradient: linear, 70% A, 3 min isocratic, in 12 min to 40% A; 6 mg of crude per injection. 22 mg (47%) of 17 (RT 9.2 min) as a colourless solid were obtained after lyophilization.

$^1$H-NMR (DMSO-$d_6$) δ 0.77–0.91 (m, 2H), 1.06–1.25 (m, 4H), 1.29–1.36 (m, 1H), 1.37–1.44 (m, 1H), 1.52–1.80 (m, 9H), 1.82 (s, 3H), 1.99–2.13 (m, 4H), 2.16–2.33 (m, 2H), 2.42 (dd, J=8.8, 16.6 Hz, 1H), 2.49 (under DMSO, m, 1H), 4.08 (m, 2H), 4.21 (m, 1H), 4.33 (m, 1H), 4.37 (d, J=10.3 Hz, 1H), 4.47 (m, 1H), 5.21 (app. t, J=9.4 Hz, 1H), 5.99 (dt, J=4.6, 56.3 Hz, 1H), 7.05–7.40 (m, 10H), 7.65 (d, 1H, J=7.7 Hz, 1H), 7.78 (d, 1H, J=7.9 Hz, 1H), 7.87 (d, 1H, J=3.4 Hz, 1H), ), 7.96 (d, 1H, J=7.8 Hz, 1H), 8.14 (d, 1H, J=7.7 Hz, 1H), 8.30 (d, 1H, J=8.10 Hz, 1H), 11.90–12.30 (bs, 4H); MS m/z 929 ($M^+$−H).

Example 4

Synthesis of Compound 1c i) 1,1-Difluoro-2-trifluoromethanesulfonyloxyethane

Triflic anhydride (120 g, 0.427 mol) was dissolved in anhydrous dichloromethane (70 mL) and cooled to −60° C. A solution of triethylamine (59.5 mL, 0.427 mol) and difluoroethanol (35 g, 0.427 mol) in dichloromethane (70 mL) was added slowly, so that the internal temperature did not exceed −50% C. After complete addition the resulting yellow solution was allowed to reach room temperature. Dichloromethane was distilled off under atmospheric pressure, and the remaining liquid fractionally distilled under reduced pressure (70–80 mbar), using a 20 cm Vigreux column to give the title sulfonate (86.2 q, 94%) (b.p.: 58–60° C.). $^1$H-NMR (CDCl$_3$) δ 4.58 (dt, J=3.6, 12.8 Hz, 2H), 6.05 (tt, J=3.6, 54 Hz, 1H); $^{19}$F—NMR (CDCl$_3$) δ −74.6 (s), −127 (s).

ii) Diethylacetamido-2-(2',2'-difluoroethyl) malonate

Diethyl acetamido malonate (35.8 g, 0.165 mol) was dissolved in anhydrous THF (300 mL) and treated with potassium tert-butanolate (18.5 g, 0.165 mol) under vigorous stirring. The resulting suspension was refluxed for 1.5 h, and the above sulfonate (40 g, 0.187 mol) was added carefully via syringe to the refluxing suspension. The solution became homogeneous and was refluxed for another 3 h. The solution was concentrated, and the residue dissolved in ethyl acetate and washed with hydrochloric acid (0.5 N, 2×), water (2×), saturated aqueous NaHCO$_3$, sodium hydroxide (1 N, 1×) and brine. Drying (Na$_2$SO$_4$) and evaporation left an orange oil, which was dissolved in diethyl ether (250 mL). The flask was kept at −20° C. overnight. 32.6 g (70%) of a colourless solid was collected; mp 72–73° C. $^1$H-NMR (CDCl$_3$) δ 1.26 (t, J=7.1 Hz, 6H), 2.05 (s, 3H), 2.98 (dt, J=4.7, 16.5 Hz, 2H), 4.27 (q, J=7.1 Hz, 4H), 5.85 (tt, J=4.7, 55.8 Hz, 1H), 6.90 (bs, 1H); $^{13}$C-NMR (CDCl$_3$) δ 13.8, 22.9, 36.8 (t, J=22.6 Hz), 62.8, 63.1, 115.2 (t, J=239 Hz), 167.0, 169.7; $^{19}$F-NMR (CDCl$_3$) δ −116.8 (s); MS m/z 282 ($M^+$+H).

iii) (R,S)-2-Amino-4,4-difluorobutanoic acid hydrochloride

The malonate prepared above (32 g, 0.114 mol) was refluxed in 500 mL hydrochloric acid (6 N) overnight. The aqueous phase was extracted with diethyl ether and then evaporated to give the title compound (19.9 g; quantitative yield) as a colourless solid; mp 164–165° C. $^1$H-NMR (D$_2$O) δ 2.35–2.70 (m, 2H), 4.27 (dd, J=Hz, 1H), 6.19 (tt, J=Hz, 1H); $^{13}$C-NMR (D$_2$O) δ 34.0 (t, J=22.2 Hz), 48.2, 115.7 (t, J=238 Hz), 171.4; $^{19}$F-NMR (D$_2$O) δ −112.7 (d, 287 Hz), −114.2 (d, 287 Hz); MS m/z 149 ($M^+$+H).

iv) (R,S)-(2-N-(tert-Butoxycarbonyl)-amino)-4,4-difluorobutyric N-methyl-O-methylcarboxamide 1.0 g (5.7 mmol) of (R,S)-2-amino-4,4-difluoro butanoic acid hydrochloride was converted to its Boc derivative using di-tert.-butyl dicarbonate (1.24 g, 5.7 mmol). After extractive workup 1.16 g (85%) of a colourless solid was obtained., which was used without further purification; mp 127–129° C. $^1$H-NMR (DMSO-$d_6$) δ 1.37 (s, 9H), 2.15 (m, 2H), 4.03 (m, 1H), 6.07 (tt, J=4.5, 56 Hz, 1H), 7.30 (d, J=8.5 Hz, 1H), 12.80 (bs, 1H); $^{13}$C-NMR (DMSO-$d_6$) δ 28.0, 35.0 (t, J=22 Hz), 48.4, 78.3, 116.0 (t, J=238 Hz), 155.3, 172.5; $^{19}$F-NMR (DMSO-$d_6$) δ −115.0 (d, J=282 Hz), −115.7 (d, J=282 Hz); MS m/z 240 ($M^+$+H).

To a solution of the Boc derivative prepared above (1.59 g, 6.65 mmol), EDC (1.40 g, 7.32 mmol) and HOBt (1.08 g, 7.98 mmol) in anhydrous dichloromethane (30 mL) was added a solution of N,O-dimethylhydroxylamine hydrochloride (714 mg, 7.32 mmol) and diisopropylethylamine (1.74 mL, 9.98 mmol) in dichloromethane (20 mL) at 0° C. After stirring at room temperature for 3 days, some dichloromethane was removed under reduced pressure. The resulting solution was diluted with ethyl acetate (150 mL) and washed successively with 1 N HCl (2×), sat. aqueous NaHCO$_3$ (2×) and brine. The organic extract was dried (Na$_2$SO$_4$) and concentrated in vacuo to give the title compound (1.81 g; 96%) of as a colourless solid. A small sample was recrystallized for analytical purposes: mp 81–82° C. $^1$H-NMR (CDCl$_3$) δ 1.44 (s, 9H), 1.93–2.44 (m, 2H), 3.23 (s, 3H), 3.76 (s, 3H), 4.84 (m, 1H), 5.39 (bd, J=9.0 Hz, 1H), 5.95 (ddt, J=3.6, 5.8, 56.0 Hz, 1H); $^{13}$C-NMR (CDCl$_3$) δ 28.3, 32.3, 37.6 (t, J=22 Hz), 46.3, 61.7, 80.2, 115.3 (t, J=239 Hz), 155.3, 171.2; $^{19}$F-NMR (CDCl$_3$) δ −114.6 (d, J=287 Hz), −115.5 (d, J=287 Hz); MS m/z 283 ($M^+$+H).

(v) (R,S)-2-(N-tert.-Butoxycarbonyl)amino-4,4-difluorobutyraldehyde dimethylacetal To a solution of the above compound (4.89 g, 17.32 mmol) in tetrahydrofuran (100 mL) was added neat diisobutylaluminum hydride (6.79 mL, 38.11 mmol) dropwise at −78° C. The solution was stirred for 2.5 h at this temperature, then methanol (5 mL) was added dropwise and the cooling bath removed. The solution was diluted with ethyl acetate (500 mL) and then washed successively with ice-cold 1 N HCl (150 mL, 3×), 2 N aqueous Rochelle's salt (150 mL) and brine (2×). Drying of the organic extract (Na$_2$SO$_4$) and evaporation in vacuo gave 3.47 g (90%) of (R,S)-2-(N-tert.-Butoxy carbonyl)-amino-4,4-difluoro butyraldehyde as an opaque oil, which was used in the next step without further purification. $^1$H-NMR (CDCl$_3$) δ 1.47 (s, 9H), 2.25 (m, 1H), 2.55 (m, 1H), 4.31 (m, 1H), 5.33 (bs, 1H), 6.03 (dt, J=6.0, 56 Hz, 1H), 9.60 (s, 1H).

1.8 g (8.06 mmol) of the crude aldehyde were converted into the dimethylacetal using trimethylorthoformate (12.4 mL, 112.9 mmol) and p-toluenesulfonic acid (154 mg, 0.81 mmol) in anhydrous methanol (30 mL). After stirring overnight at room temperature, TLC (petrolether/ethyl acetate 2:1) indicated complete consumption of the aldehyde. Saturated aqueous NaHCO$_3$ was added and the methanol evaporated under reduced pressure. The residue was dissolved with ethyl acetate (200 mL) and washed successively with saturated aqueous NaHCO$_3$ and brine. Drying (Na$_2$SO$_4$) and evaporation left an oil which was purified by flash chromatography (160 g silica gel, petrolether/ethyl acetate 4:1, containing 0.5% triethylamine), to give the title compound (1.44 g; 66%) as a colourless solid; mp 61–62° C. $^1$H-NMR (CDCl$_3$) δ 1.48 (s, 9H), 1.86–2.05 (m, 1H), 2.09–2.27 (m, 1H), 3.44 (s, 3H), 3.45 (s, 3H), 3.99 (m, 1H), 4.25 (d, J=3.0 Hz, 1H), 4.76 (bd, J=8.0 Hz, 1H), 5.96 (ddt, J=4.0, 5.4, 56.6 Hz, 1H); $^{13}$C-NMR (CDCl$_3$) δ 28.3, 34.4 (t, J=22 Hz), 47.6, 55.9, 56.5, 79.8, 105.6, 116.3 (t, J=238 Hz), 155.5; $^{19}$F-NMR (CDCl$_3$) δ −114.6 (d, J=284 Hz), −115.5 (d, J=284 Hz); MS m/z 270 (M$^+$+H).

vi) (R,S)-2-Amino-4,4-difluorobutyraldehyde dimethylacetal hydrochloride

To 440 mg (1.63 mmol) of the above acetal was added a solution of gaseous HCl in anhydrous methanol (10% HCl by weight, 15 mL) at 0° C. The solution was stirred at this temperature for 10 min, then the ice-bath was removed. After 20 min at ambient temperature TLC indicated complete consumption of the acetal to baseline material. The reaction mixture was evaporated to dryness, then triturated with n-pentane. Drying under high vacuum produced 310 mg (93%) of 13 an light brown hygroscopic solid, which was pure by $^1$H-NMR (400 MHz) and used without further purification. $^1$H-NMR (DMSO-d$_6$) δ 2.13–2.23 (m, 2H), 3.32–3.37 (m, 1H), 3.40 (s, 3H), 3.41 (s, 3H), 4.56 (d, J=4.7 Hz, 1H), 6.33 (tt, J=4.8, 56.2 Hz, 1H), 8.45 (bs, 3H); $^{13}$C-NMR (DMSO-d$_6$) δ 32.6 (t, J=22.6 Hz), 47.0, 55.8, 55.9, 102.8, 115.5 (t, J=235.3 Hz); $^{19}$F-NMR (DMSO-d$_6$) δ −113.8 (d, J=283 Hz), −114.7 (d, J=283 Hz); MS m/z 206 (M$^+$+H).

vii) (1c)

220 mg of the protected pentapeptide (Ac-tert-butyl-asp-tert-butyl-glu-diphenylalanine-tert-butyl-glu-cyclohexylala) (0.225 mmol) were dissolved in 1 mL chloroform. EDC (52 mg, 0.27 mmol) and HOBt (61 mg, 0.45 mmol) were added and the solution cooled to 0° C. (±2-Amino-4,4-difluorobutyraldehyde dimethylacetal hydrochloride (from vi above) (80 mg, 0.39 mmol) was dissolved in chloroform (0.8 mL) containing diisopropylethyl amine (0.47 mmol, 0.082 mL) and the resulting solution was added via syringe to the pentapeptide. Another 0.3 mL chloroform was used to rinse flask and syringe. The cooling bath was removed after 10 min and the orange solution stirred for 3 h. Analytical HPLC indicated complete conversion of the pentapeptide. The reaction was taken into a mixture of ethyl acetate and dichloromethane (150 mL, 3:1) and washed successively with 0.1 M aqueous KHSO$_4$, (3×80 mL), water (2×100 mL), saturated aqueous NaHCO$_3$ and brine (2×100 mL). Drying (Na$_2$SO$_4$) and evaporation gave a brown solid which was immediately deprotected with a solution of trifluoroacetic acid, dichloromethane and water (60/35/5, v/v/v; 50 mL). After 30 min at room temperature the solvents were evaporated in vacuo and the remaining brown solid (252 mg) was separated by preparative HPLC (Nova-Pak Prep column). Flow 40 mL/min; Gradient: linear, 70% A, 2 min isocratic, in 18 min to 60% A; 20 mg of crude per injection.

First fraction: RT: 9.4 min, 54 mg (26%) of a colourless powder after lyophilization; 1 diastereomer, 94% pure by analytical HPLC (gradient 1, 6.77 min; gradient 2, 6.45 min). In the $^1$H-NMR 10–20% of the aldehyde was hydrated. Addition of water gave a ratio of aldehyde to hydrate of 1:9. Only data for the aldehyde are reported. $^1$H-NMR (DMSO-d$_6$) δ 0.77–0.94 (m, 2H), 1.05–1.31 (m, 4H), 1.32–1.50 (m, 2H), 1.52–1.78 (m, 9H), 1.82 (s, 3H), 1.95–2.15 (m, 6H), 2.36–2.46 (m, 2H), 4.00–4.06 (m, 2H), ), 4.12–4.23 (m, 2H), 4.39 (d, J=10.3 Hz, 1H), 4.47 (m, 1H), 5.19 (app. t, J=9.4 Hz, 1H), 6.10 (dt, J=4.6, 56.0 Hz, 1H), 7.05–7.38 (m, 10H), 7.75 (d, J=7.3 Hz, 1H), 7.81 (d, J=6.9 Hz, 1H), 7.86 (d, J=8.0 Hz, 1H), 8.10 (m, 2H), 8.40 (d, J=7.2 Hz, 1H), 9.26 (s, 1H), 11.50–12.50 (bs, 3H); MS m/z 915 (M$^+$+H).

Second fraction: RT: 12.2 min, 42 mg (20%), colourless powder after lyophilization;

$^1$H-NMR (DMSO-d$_6$) δ 0.76–0.94 (m, 2H), 1.05–1.30 (m, 4H), 1.32–1.50 (m, 2H), 1.52–1.78 (m, 9H), 1.83 (s, 3H), 1.95–2.15 (m, 6H), 2.25–2.45 (m, 2H), 3.98–4.12 (m, 2H), ), 4.15–4.23 (m, 2H), 4.35–4.51 (m, 2H), 5.15–5.19 (m, 1H), 6.06 (dt, J=4.5, 56.1. Hz, 1H), 7.07–7.38 (m, 10H), 7.58 (d, J=7.5 Hz, 1H), 7.60–8.12 (m, 4H), 8.43 (bs, 1H), 9.32 (s, 1H), 11.90 (bs, 3H); MS m/z 915 (M$^+$+H).

Example 5

Synthesis of Compound 1d i) (R,S)-4-(tert.-Butyloxycarbonylamino)-6,6-difluoro-3-oxo-2-triphenylphosphoranylidene-hexanenitrile Using the method described by Wassermann et al in Journal of Organic Chemistry (1994), 4366, (±)-N-(tert-Butyloxycarbonyl)-2-amino-4,4-difluorobutyric (1.0 g, 4.18 mmol, prepared as described in example 4 (iv), EDC (841 mg, 4.39 mmol) and N,N-dimethylaminopyridine (51 mg, 0.42 mmol) were dissolved in dichloromethane (25 mL) and cooled to 0° C. A solution of triphenylphosphoranyliden nitrile (2.52 g, 8.36 mmol) in dichloromethane (16 mL) was added dropwise. After the addition the reaction was allowed to reach room temperature and stirred for 6 h. Then ethyl acetate (150 mL) was added and the solution washed successively with 0.5 M aqueous KHSO$_4$, water and brine (2×100 mL). Drying (Na$_2$SO$_4$) and evaporation gave an orange solid, which was purified by flash chromatography on silica gel (PE/ethyl acetate 2:1 to 1.5:1). 1.21 g (54%) of a colorless solid were obtained; m.p. 194–195° C. (n-heptane/dichloromethane). $^1$H-NMR (CDCl$_3$) δ 1.41 (s, 9H), 2.12–2.28 (m, 1H), 2.38–2.70 (m, 1H), 5.00 (m, 1H), 5.41 (bs, 1H), 5.92 (tt, J=4.5, 56.2 Hz, 1H), 7.41–7.78 (m, 15H); $^{19}$F-NMR (CDCl$_3$) δ −113.8 (d, J=287 Hz), −114.1 (d, J=287 Hz); MS m/z 523 (M$^+$+H).

ii) (±)-Methyl-3-(tert.-butyloxycarbonylamino)-5,5-difluoro-2-hydroxy-pentanoate The foregoing compound (700 mg, 1.34 mmol) was dissolved in dichloromethane/methanol (13 ml, 7:3, v/v) and cooled to −78° C. Ozone was bubbled through the solution until the blue color remained. The solution was then purged with nitrogen and stirred at room temperature for 4 h. Evaporation gave a light yellow oil, which was dissolved in methanol (10 mL) and cooled to 0° C. Solid sodium tetrahydroborate (146 mg, 3.86 mmol) was added portionwise. After 30 min ethyl acetate (50 mL) was added followed by 0.5 N HCl (5 mL). After stirring the mixture for 5 min, the organic phase was separated, washed with 1 N HCl, water and brine. Drying (Na$_2$SO$_4$) and evaporation gave a yellow oil, which was purified by flash chromatography on silica gel (PE/ethyl acetate 2.5:1) 0.182 mg (50%) of a colorless waxy solid were obtained. 2 diastereomers (1.5:1). For analytical purposes some fractions containing the single diastereomers were collected.

1. Fraction (major diastereomer), m.p. 103–104° C. (n-pentane/CH$_2$Cl$_2$). $^1$H-NMR(CDCl$_3$) δ 1.41 (s, 9H), 2.10–2.23 (m, 2H), 3.32 (d, J=4.4 Hz, 1H), 3.81 (s, 3H), 4.20 (dd, J=1.6, 4.4 Hz, 1H), 4.33 (m, 2H), 4.87 (d, J=9.8 Hz, 1H), 5.96 (tt, J=4.5, 56.1 Hz, 1H); $^{13}$C-NMR (CDCl$_3$) δ 28.2, 37.1 (t, J=22.5 Hz), 48.3, 53.0, 72.3, 80.2, 115.7 (t, J=238 Hz), 155.1, 173.2; $^{19}$F-NMR (CDCl$_3$) δ −114.4 (d, J=287 Hz), −115.1 (d, J=287 Hz); MS m/z 283 (M$^+$+H).

2. Fraction (minor diastereomer), m.p. 118–119° C. (n-pentane/CH$_2$Cl$_2$). $^1$H-NMR (CDCl$_3$) δ 1.45 (s, 9H), 1.78–1.85 (n, 1H), 2.02–2.11 (m, 1H), 3.17 (bs, 1H), 3.84 (s, 3H), 4.26 (bm, 1H), 4.35 (bs, 1H), 4.97 (d, J=8.2 Hz, 1H), 5.94 (ddt, J=3.3, 5.9, 56.2 Hz, 1H); $^{13}$C-NMR (CDCl$_3$) δ 28.3, 34.6 (t, J=21.2 Hz), 48.6, 53.1, 72.8, 80.3, 115.8 (t, J=238 Hz), 155.3, 172.7; $^{19}$F-NMR (CDCl$_3$) δ −114.0 (d, J=286 Hz), −114.8 (d, J=286 Hz); MS m/z 283 (M$^+$+H).

iii) (R,S)-Methyl-3-amino-5,5-difluoro-2-hydroxy-pentanoate hydrochloride 1.54 g (5.46 mmol) of the diastereomeric mixture of the foregoing compound were treated with a solution of gaseous hydrochloric acid in ethyl acetate (3 M, 36 mL) at 0° C. After 30 min the cooling bath was removed and the solution stirred at room temperature for 1.5 h. Evaporation gave the title compound as a yellow solid, 1.19 g (100%); 2 diastereomers: 1.3:1*). $^1$H-NMR (DMSO-d$_6$) δ 1.95–2.36 (m, 1H), 3.47–3.61 (m, 1H), 3.68, 3.69* (s, 3H), 4.36 (d, J=3.6 Hz, 1H), 4.58* (d, J=2.5 Hz, 1H), 6.32* (ddt, J=3.6, 5.7, 56 Hz, 1H), 6.36 (dt, J=4.7, 55.8 Hz, 1H), 6.45*, 6.69 (bs, 1H), 8.41, 8.60* (bs, 3H); $^{13}$C-NMR (DMSO-d$_6$) δ 32.4*, 33.8 (t, J=22.3*, 22.2 Hz), 47.6*, 47.7, 52.15*, 52.2, 69.0, 69.7*, 115.4 (t, J=236 Hz), 170.8; $^{19}$F-NMR (DMSO-d$_6$) δ −114.3*, −114.6 (d, J=284 Hz), −115.2*, −115.6 (d, J=284 Hz); MS m/z 183 (M$^+$+H, free amine).

iv) (1d)

150 mg pentapeptide (0.153 mmol) were dissolved in dimethylformamide (2 mL). HATU (64 mg, 0.17 mmol) and 2,6-lutidine (49 mg, 0.46 mmol) were added and the solution cooled to 0° C. (±)-Methyl-3-amino-5,5-difluoro-2-hydroxy-pentanoate hydrochloride (40 mg, 0.18 mmol; prepared as above) was added as a solid. The cooling bath was removed after 30 min and the resulting solution stirred overnight. The reaction was taken into a mixture of ethyl acetate and dichloromethane (150 mL, 3:1) and washed successively with 1 M aqueous KHSO$_4$, (3×80 mL), water (2×100 mL), saturated aqueous NaHCO$_3$ and brine (2×100 mL). Drying (Na$_2$SO$_4$) and evaporation gave a solid which was oxidized with Dess-Martin periodinane (195 mg, 0.46 mmol) in dichloromethane (3 mL) and tert.-butanol (34 mg, 0.46 mmol). After stirring at room temperature for 24 h, ethyl acetate (50 mL) was added. The organic phase was washed 3× with a mixture of aqueous saturated sodium hydrogen carbonate and aqueous saturated sodium thiosulfate (1:1, v/v), then with brine. Drying (Na$_2$SO$_4$) and evaporation gave a solid which was deprotected with a solution of trifluoroacetic acid, dichloromethane and water (50/45/5, v/v/v; 20 mL). After 30 min at room temperature the solvents were evaporated in vacuo and the remaining solid (158 mg) dissolved in methanol (4 mL). Aqueous sodium hydroxide (1 mL, 1 N) was added and the solution left at room temperature for 15 min. Then aqueous hydrochloric acid (1 mL, 1 N) was added and the solution diluted with water/acetonitrile (70/30, v/v) and lyophilized. The product was isolated by preparative HPLC (Nova-Pak Prep). Flow 35 mL/min; Gradient: linear, 75% A, 5 min isocratic, in 10 min to 50% A; 20 mg of crude per injection.

First fraction: RT: 12.8 min, 50 mg (34%) of a colorless powder after lyophilization; 1 diastereomer, 99% pure by analytical HPLC (gradient 1, 6.9 min; gradient 2, 6.45 min). In the $^1$H-NMR 15–20% of the ketoacid was hydrated. Addition of water gave a ratio of ketoacid to hydrate of 1:1. Only data for the ketoacid are reported. $^1$H-NMR (DMSO-d$_6$) δ 0.77–0.92 (m, 2H), 1.05–1.43 (m, 6H), 1.52–1.78 (m, 9H), 1.82 (s, 3H), 1.97–2.17 (m, 5H), 2.30–2.50 (m, 3H), 4.02–4.19 (m, 3H), 4.37 (d, J=10.3 Hz, 1H), 4.49 (m, 1H), 4.92 (m, 1H), 5.21 (app. t, J=9.3 Hz, 1H), 6.08 (ddt, J=3.3, 5.5, 56.0 Hz, 1H), 7.03–7.38 (m, 10H), 7.72 (d, J=7.3 Hz, 1H), 7.78 (d, J=7.7 Hz, 1H), 7.85 (d, J=8.4 Hz, 1H), 7.90 (d, J=7.9 Hz, 1H), 8.12 (d, J=7.6 Hz, 1H), 8.49 (d, J=7.0 Hz, 1H); MS m/z 959.9 (M$^+$+H).

Second fraction: RT: 13.9 min, 51 mg (34%), colorless powder after lyophilization; 1 diastereomer, 97% pure by analytical HPLC (gradient 1, 7.3 min). $^1$H-NMR (DMSO-d$_6$) δ 0.73–0.98 (m, 2H), 1.05–1.50 (m, 6H), 1.52–1.84 (m, 9H), 1.84 (s, 3H), 1.97–2.22 (m, 5H), 2.30–2.50 (m, 3H), 4.03–4.26 (m, 3H), 4.39 (d, J=10.2 Hz, 1H), 4.49 (m, 1H), 4.74 (m, 1H), 5.21 (app. t, J=9.2 Hz, 1H), 6.06 (ddt, J=3.6, 5.4, 56.4 Hz, 1H), 7.03–7.38 (m, 10H), 7.69 (d, J=7.5 Hz, 1H), 7.79 (d, J=7.8 Hz, 1H), 7.82 (d, J=8.4 Hz, 1H), 7.89 (d, J=8.1 Hz, 1H), 8.13 (d, J=7.8 Hz, 1H), 6.59 (d, J=6.9 Hz, 1H); MS m/z 959.6 (M$^+$+H).

Example 6

Synthesis of Compound (2a)

The protected tripeptide shown below (Ac-Diphenylala-tert-butyl-Glu-β-Cyclohexylala) was employed in this example.

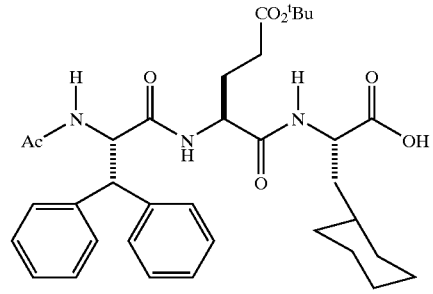

200 mg tripeptide (0.32 mmol) and HATU (129 mg, 0.34 mmol) were dissolved in dimethylformamide (2 mL) and the solution cooled to 0° C. (±)-Methyl-3-amino-5,5-difluoro-2-hydroxy-pentanoate hydrochloride (77 mg, 0.35 mmol, prepared as described in example 5 (iii)) in DMF (1 mL) and: 2,6-lutidine (103 mg, 0.96 mmol) were added and the solution allowed to reach room temperature and stirred overnight. The reaction was taken into ethyl acetate (60 mL) and washed successively with 1 M aqueous KHSO$_4$, (2×30 mL), water, saturated aqueous NaHCO$_3$ and brine (2×30 mL each). Drying (Na$_2$SO$_4$) and evaporation gave a 235 mg of a solid. 231 mg of this material were oxidized with Dess- Martin periodinane (374 mg, 0.88 mmol) in dichloromethane (2 mL) and tert.-butanol (65 mg, 0.88 mmol). After stirring at room temperature for 3 h, analytical HPLC indicated complete conversion of the starting material. Ethyl acetate (100 mL) was added. The organic phase was washed 2× with a mixture of aqueous saturated sodium hydrogen carbonate and aqueous saturated sodium thiosulfate (1:1, v/v, 50 mL), then with brine. Drying ($Na_2SO_4$) and evaporation gave 220 mg of a colorless solid which was deprotected with a solution of trifluoroacetic acid, dichloromethane and water (60/35/5, v/v/v; 20 mL). After 30 min at room temperature the solvents were evaporated in vacuo to give a light yellow solid (221 mg). 150 mg of this material were dissolved in methanol (4 mL) and aqueous sodium hydroxide (1 mL, 1 N) was added. The solution was left at room temperature for 20 min. Then aqueous hydrochloric acid (1 mL, 1 N) was added and the solution diluted with water/acetonitrile (70/30, v/v, 15 mL) and lyophilized. The product was isolated by preparative HPLC (Nova-Pak Prep). Flow 30 mL/min; Gradient: linear, 70% A, 5 min isocratic, in 13 min to 44% A; 10–12 mg of crude per injection. First fraction; RT: 13.6 min, 21 mg (14%) of a colorless powder after lyophilization; 1 diastereomer, 99% pure by analytical HPLC (gradient 1, 7.34 min, gradient 2, 7.72 min). In the $^1$H-NMR 10–15% of the ketone was hydrated. Addition of water increased the ratio of ketoacid to hydrate to 1:1. Only data for the ketoacid are reported. $^1$H-NMR (DMSO-$d_6$) δ 0.73–0.91 (m, 2H), 1.02–1.24 (m, 4H), 1.24–1.43 (m, 2H), 1.52–1.70 (m, 6H), 1.65 (s, 3H), 1.71–1.82 (m, 1H), 1.96–2.08 (m, 2H), 2.08–2.23 (m, 1H), 2.28–2.40 (m, 1H), 4.06 (Im 1H), 4.15 (m, 1H), 4.32 (d, J=11.1 Hz, 1H), 4.92 (m, 1H), 5.22 (dd, J=8.7, 11.1 Hz, 1H), 6.08 (ddt, J=3.6, 5.7, 55.9 Hz, 1H), 7.04–7.32 (m, 10H), 7.72 (d, J=7.4 Hz, 1H), 7.87 (d, J=8.1 Hz, 1H), 8.15 (d, J=8.7 Hz, 1H), 8.54 (d, J=7.1 Hz, 1H); MS m/z 715 (M$^+$+H).

Second fraction: RT: 14.8 min, 23 mg (15%), colorless powder after lyophilization; $^1$H-NMR (DMSO-$d_6$) δ 0.74–0.93 (m, 2H), 1.04–1.24 (m, 4H), 1.24–1.43 (m, 2H), 1.52–1.70 (m, 6H), 1.65 (s, 3H), 1.71–1.82 (m, 1H), 1.96–2.08 (m, 2H), 2.08–2.21 (m, 1H), 2.28–2.39 (m, 1H), 4.07 (m, 1H), 4.16 (m, 1H), 4.32 (d, J=11.1 Hz, 1H), 4.73 (m, 1H), 5.21 (dd, J=8.7, 11.1 Hz, 1H), 6.06 (ddt, J=3.6, 5.5, 56.4 Hz, 1H), 7.04–7.32 (m, 10H), 7.69 (d, J=7.5 Hz, 1H), 7.88 (d, J=8.0 Hz, 1H), 8.15 (d, J=8.6 Hz, 1H), 8.70 (d, J=7.0 Hz, 1H); MS m/z 715 (M$^+$+H).

Example 7

Synthesis of Compound 3c i) (R,S)-4-Amino-6,6-difluoro-3-oxo-2-triphenylphosphoranylidene-hexanenitrile A solution of (±)-N-(Benzyloxycarbonyl)-2-amino-4,4-difluorobutyric acid (4.22 g, prepared as described in example 3 (iv), but using racemic difluoroaminobutyric acid), EDC (3.25 g, 16.94 mmol) and HOBt (2.49 g, 18.48 mmol) in dichloromethane (150 mL) was cooled to 0° C. A solution of triphenylphosphoranyliden nitrile (10.2 g, 33.97 mmol) was added dropwise over 2 h. After addition, the cooling bath was removed and the mixture stirred at room temperature for 24 h. The reaction mixture was washed successively with 1 N aqueous HCl, water, saturated aqueous $NaHCO_3$ and brine. Drying ($Na_2SO_4$) and evaporation gave a solid, which was recrystallized from petrol ether/ethyl acetate to give 6.58 g of (±)-4-(N-(Benzyloxycarbonyl-amino)-6,6-difluoro-3-oxo-2-triphenylphosphoranylidene-hexanenitrile as a colorless powder. The mother liquor was evaporated and the solid separated by flash column chromatography on silica gel (toluene/ethyl acetate 2:1) to yield another 441 mg (combined yield 82%). $^1$H-NMR (DMSO-$d_6$) δ 2.01–2.23 (m, 1H), 2.26–2.45 (m, 1H), 4.73 (m, 1H), 5.03 (d, J=12.6 Hz, 1H), 5.09 (d, J=12.6 Hz, 1H), 6.08 (ddt, J=3.6, 5.7, 56.6 Hz, 1H), 7.25–7.44 (m, 5H), 7.48–7.70 (m, 13H), 7.72–7.80 (m, 3H); $^{19}$F-NMR (DMSO-$d_6$) δ –114.6 (d, J=282 Hz), –115.7 (d, J=282 Hz); MS m/z 557 (M$^+$+H).

3.00 g (5.34 mmol) of the foregoing compound and palladium on carbon (10% Pd, 6.0 g) were placed in a 500 mL flask. Methanol (150 mL) was added slowly under nitrogen, followed by ammonium acetate (4.0 g). The reaction was stirred at room temperature for 30 min, when thin layer chromatography (5% triethylamine in ethyl acetate) indicated complete conversion of starting material. The palladium catalyst was removed by filtration and washed extensively with ethyl acetate (500 mL). The filtrate was washed with aqueous saturated sodium hydrogencarbonate (2×200 mL) and brine. Drying ($Na_2SO_4$) and evaporation gave 1.90 g (84%) of the title compound as a colorless solid. %). $^1$H-NMR (DMSO-$d_6$) δ 1.73–1.88 (m, 3H), 2.09–2.23 (m, 1H), 3.94 (dd, J=4.1, 9.8 Hz, 1H), 6.13 (ddt, J=2.8, 6.8, 57.1 Hz, 1H), 7.55–7.69 (m, 12H), 7.70–7.78 (m, 3H); $^{19}$F-NMR (DMSO-$d_6$) d –114.8 (d, J=280 Hz), –115.8 (d, J=280 Hz); MS m/z 423 (M$^+$+H).

ii) (3c)

The protected dipeptide shown below (Cbz-Ile-LeuOH) was used in this example.

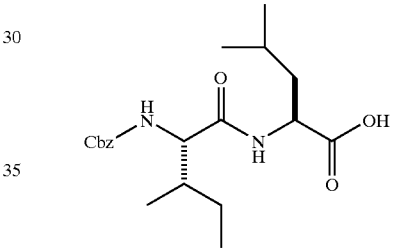

The dipeptide (184 mg, 0.49 mmol) was dissolved in dichloromethane (4 mL) and EDC (102 mg, 0.54 mmol) and HOBt (72 mg, 0.54 mg) were added. The resulting solution was cooled to 0° C. and (±)-4-Amino-6,6-difluoro-3-oxo-2-triphenylphosphoranylidene-hexanenitrile (226 mg, 0.54 mmol) was added in one portion. The ice bath was removed and the mixture stirred at room temperature for 90 min. The reaction mixture was diluted with ethyl acetate and washed successively with 1 N aqueous HCl, water, saturated aqueous $NaHCO_3$ and brine. Drying ($Na_2SO_4$) and evaporation gave a solid which was purified by flash chromatography (PE/ethyl acetate 1:2) to give 319 mg (83%) of Cbz-Ile-Leu-difluoro-3-oxo-2-triphenylphosphoranylidene-hexanenitrile as a colorless powder (mixure of diastereomers, 2:1*). $^1$H-NMR (DMSO-$d_6$) δ 0.72–0.88 (m, 12H), 1.04–1.15 (m, 1H), 1.34–1.49 (m, 3H), 1.52–1.63 (m, 1H), 1.63–1.76 (m, 1H), 2.00–2.22 (m, 1H), 2.26–2.43 (m, 1H), 3.88 (app. t, J=8.1 Hz, 1H), 4.30 (dd, J=8.2, 14.6 Hz, 1 H), 4.36* (dd, J=8.2, 15.6 Hz, 1H), 4.92–5.10 (m, 3H), 5.97, 5.99* (m, 1H), 7.23–7.40 (m, 5H), 7.51–7.68 (m, 12H), 7.69–7.77 (m, 3H), 7.89* (d, J=8.5 Hz, 1H), 7.94 (d, J=8.0 Hz, 1H), 8.07* (d, J=7.9 Hz, 1H), 8.18 (d, J=7.9 Hz, 1H). MS m/z 783 (M$^+$+H).

The foregoing compound (210 mg, 0.27 mmol) was dissolved in dichloromethane/methanol (6 ml, 7:3, v/v) and cooled to –78° C. Ozone was bubbled through the solution until the blue color remained. The solution was then purged with nitrogen and stirred at room temperature for 2 h.

Evaporation gave a light yellow oil, which purified by flash chromatography (PE/ethylacetate 1:1) to yield 103 mg (68%) of a colorless solid, which was dissolved in methanol (3 mL). Aqueous sodium hydroxide (1 N, 1 mL) was added and the solution stirred at room temperature for 30 min. After addition of hydrochloric acid (1 N, 1 mL), the mixture was diluted with water/acetonitrile (80:20, v/v). The product was isolated by preparative RP-HPLC (Waters Symmetry). Flow 17 mL/min; Gradient: linear, 70% A, 3 min isocratic, in 15 min to 40%.

First fraction: RT: 13.1 min, 8 mg (8%) of a colorless powder after lyophilization; 1 diastereomer. $^1$H-NMR (DMSO-$d_6$) δ 0.75–0.91 (m, 12H), 1.02–1.24 (m, 1H), 1.34–1.47 (m, 3H), 1.55–1.77 (m, 2H), 2.02–2.20 (m, 1H), 2.29–2.40 (m, 1H), 3.89 (app. t, J7=8.2 Hz, 1H), 4.28 (dd, J=7.3, 15.4 Hz, 1H), 4.93 (m, 1H), 5.02 (d, J=5.7 Hz, 2H), 6.04 (tt, J=3.2, 57.0 Hz, 1H), 7.32–7.40 (m, 6H), 7.96 (d, J=7.6 Hz, 1H), 8.44 (bs, 1H). MS m/z 528 (M$^+$+H).

The second fraction contained a 1:1 mixture of the two diastereomers (34 mg, 34%).

Example 8

Synthesis of 5j i) Leucine-6,6-difluoro-3-oxo-2-triphenyl-phosphoranylidene-pentanenitrile Cbz-L-Leucine (760 mg, 2.80 mmol), EDC (598 mg, 3.12 mmol) and HOBt (421 mg, 3.12 mmol) were dissolved in dichloromethane (15 mL) and cooled to 0° C. A solution of (±)-4-Amino-6,6-difluoro-3-oxo-2-triphenyl-phosphoranylidene-hexanenitrile (1.10 g, 2.60 mmol) (prepared as described in example 7, i)) in dichloromethane (13 mL) was added dropwise. The resulting mixture was stirred overnight at room temperature, then ethyl acetate (200 mL) was added and the mixture washed successively with 1 N aqueous HCl, water, saturated aqueous NaHCO$_3$ and brine. Drying (Na$_2$SO$_4$) and evaporation gave a solid, which was purified by flash chromatography (PE/ethylacetate 1:2) to afford 1.50 g of a colorless solid (2 diastereomers, 1.5:1*). $^1$H-NMR (DMSO-$d_6$) δ 0.77–0.89 (m, 6H), 1.38–1.49 (m, 2H), 1.55–1.67 (m, 1H), 2.03–2.21 (m, 1H), 2.27–2.42 (m, 1H), 4.06 (m, 1H), 4.96 (m, 1H), 5.01 (d, J=11.1 Hz, 2H), 5.95, 6.01* (m, 1H), 7.22–7.38 (m, 5H), 7.50–7.68 (m, 12H), 7.70–7.79 (m, 3H), 7.37 (d, J=8.8 Hz, 1H), 7.41* (d, J=9.0 Hz, 1H), 8.11 (d, J=7.9 Hz, 1H), 8.15* (d, J=7.8 Hz, 1H). MS m/z 670 (M$^+$+H).

To the foregoing compound (1.35 g, 2.02 mmol) and palladium on carbon (10% Pd, 2.8 g) was slowly added methanol (70 mL) under nitrogen, followed by ammonium acetate (2.0 g). The reaction was stirred at room temperature for 20 min, when thin layer chromatography (5% triethylamine in ethyl acetate) indicated complete conversion of starting material. The palladium catalyst was removed by filtration and washed extensively with ethyl acetate (300 mL). The filtrate was washed with aqueous saturated sodium hydrogencarbonate/brine (200 mL, 1/1, v/v) and then with brine. Drying (Na$_2$SO$_4$) and evaporation gave 976 mg (84%) of the title compound as a colorless solid (2 diastereomers, 1:1*). $^1$H-NMR (DMSO-$d_6$) δ 0.83 (d, J=6.5 Hz, 3H), 0.84* (d, J=6.5 Hz, 3H), 0.86 (d, J=6.5 Hz, 3H), 0.88* (d, J=6.5 Hz, 3H), 1.24–1.32 (m, 1H), 1.42–1.49 (m, 1H), 1.66–1.74 (m, 1H), 2.03–2.24 (m, 1H), 2.28–2.44 (m, 1H), 3.27 (m, 3H), 4.98 (m, 1H), 5.01 (d, J=11.1 Hz, 2H), 6.00, 6.04* (m, 1H), 7.55–7.68 (m, 12H), 7.70–7.80 (m, 3H), 7.85 (d, J=8.2 Hz, 1H), 7.52* (d, J=8.2 Hz, 1H), 8.26 (d, J=7.9 Hz, 1H), 8.36* (d, J=7.9 Hz, 1H). $^{19}$F-NMR (DMSO-$d_6$) δ −113.8, −114.0* (d, J=281 Hz), −114.7, −114.9 (d, J=281 Hz); MS m/z 536 (M$^+$+H).

ii) (5i)

To a solution of BocGlu(OBn)OH (265 mg, 0.78 mmol) in dichloromethane (8 mL) was added EDC (158 mg, 0.82 mmol) and HOBt.H$_2$O (137 mg, 0.9 mmol) at 0° C. After 10 min the foregoing compound (400 mg, 0.747 mmol) was added as a solid. After stirring overnight, the reaction was worked up as described in example 7, ii). 550 mg (0.64 mmol) of the crude product were dissolved in methanol (30 mL). Palladium on charcoal (1 g, 10% Pd) was added carefully, followed by ammonium formate (1.5 g). After 20 min workup was conducted as described in example 7, ii). An off white solid (419 mg, 85%) was obtained. 410 mg of this material were ozonized in dichloromethane (20 mL) at −78° C. After the solution turned blue, ozonization was continued until TLC (PE/ethyl acetate 1:1) indicated complete consumption of the starting material. The ozone was removed by bubbling nitrogen through the reaction and THF/water (4:1, v/v, 10 mL) was added. The cooling bath was removed and the mixture stirred at room temperature for 3 h. Evaporation gave a light yellow oil, which purified by medium pressure chromatography (acetonitrile water 3:7) using a RP C18 Lobar column (Fa. Merck KGA, Darmstadt) to yield 224 mg of a colorless powder after lyophilization. The product was isolated by preparative RP-HPLC (Waters Symmetry). Flow 17 mL/min; Gradient linear, 80% A, 3 min isocratic, in 12 min to 50%. First fraction: RT: 10.2 min, 40 mg (15%) of a colorless powder after lyophilization; 1 diastereomer. $^1$H-NMR (DMSO-$d_6$) δ 0.80–0.92 (m, 6H), 1.37 (s, 9H), 1.50–1.70 (m, 2H), 1.55–1.72 (m, 1H), 1.77–1.89 (m, 1H), 2.10–2.24 (m, 1H), 2.23 (m, 2H), 2.30–2.42 (m, 1H), 3.90 (m, 1H), 4.27 (m, 1H), 4.91 (m, 1H), 6.04 (tt, J=3.6, 56.8 Hz, 1H), 6.93 (bs, 1H), 7.84 (d, J=7.5 Hz, 1H), 8.60 (bs, 1H). MS m/z 510 (M$^+$+H).

Second fraction: RT: 11.3 min, 50 mg (18%) of a colorless powder after lyophilization; 1 diastereomer. $^1$H-NMR (DMSO-$d_6$) δ 0.78–0.90 (m, 6H), 1.37 (s, 9H), 1.50–1.70 (m, 2H), 1.55–1.72 (m, 1H), 1.77–1.89 (m, 1H), 2.10–2.24 (m, 1H), 2.23 (m, 2H), 2.30–2.42 (m, 1H), 3.90 (m, 1H), 4.27 (m, 1H), 4.70 (m, 1H), 6.03 (tt, J=3.7, 57.2 Hz, 1H), 6.94 (ds, J=7.8 Hz, 1H), 7.84 (d, J=7.6 Hz, 1H), 8.70 (bs, 1H). MS m/z 510 (M$^+$+H).

Example 9

Synthesis of Compound 9x i) Synthesis of compound 15 (see scheme 7) Boc-Leu-OH (1.16 g, 5 mmol) was dissolved in dichloromethane (50 mL) and EDC (1.05 g, 5.5 mmol) and HOBt (743 mg, 5.5 mmol) were added. The resulting solution was cooled to 0° C. and (±)-4-Amino-6,6-difluoro-3-oxo-2-triphenylphosphoranylidene-hexanenitrile (2.32 g, 5.5 mmol) was added in one portion. The ice bath was removed and the mixture stirred at room temperature overnight. The reaction mixture was diluted with dichloromethane (100 mL) and washed successively with 1 N aqueous HCl, water, saturated aqueous NaHCO$_3$ and brine. Drying (Na$_2$SO$_4$) and evaporation gave 2.7 g (85%) of Boc-Leu-6,6-difluoro-3-oxo-2-triphenylphosphoranylidene-hexanenitrile as a yellowish foam. The foregoing compound (2.7 g, 4.2 mmol) was dissolved in dichloromethane/methanol (40 ml, 7:3, v/v) and cooled to −78° C. Ozone was bubbled through the solution until the blue color remained. The solution was then purged with nitrogen and 12 mL of MeOH were added, the resulting solution was stirred at −78° C. for 30 min. and at room temperature for 2 h. Evaporation gave a light yellow oil, which was dissolved in MeOH (6 mL) and the resulting solution was cooled to 0° C. After addition portionwise of NaBH$_4$ (159 mg, 4.2 mmol) the resulting reaction mixture was stirred at 0° C. for 2 hours, poured into saturated aqueous NaHCO$_3$ and extracted with EtOAc. The combined organic layers were washed with brine and dried (Na$_2$SO$_4$). Evaporation gave a solid which was purified by flash chromatography (PE/ethyl acetate 3:2) to give 832 mg (50%) of the Boc protected dipeptide hydroxyester.

The above compound (832 mg, 2.1 mmol) was dissolved in EtOAc (8 mL) and cooled to 0° C. To the resulting solution 4 N HCl in dioxane (2.6 mL, 10.5 mmol) was added. The reaction was stirred at room temperature for 2 hours. The solvent was evaporated giving 670 mg (96%) of 15 as a pale yellow foam (mixture of four diastereomers). $^1$H-NMR (DMSO-d$_6$) δ 8.84 (d, J=8.0 Hz, 1H), 8.73 (d, J=8.9 Hz, 1H), 8.84 (br t, 2H), 8.33–8.20 (m, 8H), 6.25–5.83 (m, 4H), 4.36–4.18 (m, 4H), 3.78–3.60 (m, 4H), 3.66 (s, 3H), 3.62 (s, 6H), 3.56 (s, 3H), 2.20–1.94 (m, 8H), 1.65–1.42 (m, 9H), 0.89–0.86 (m, 24H); MS m/z 297 (M$^+$+H).

ii) Synthesis of Compound 16 (see Scheme 7)

To a solution of (±) indoline-2-carboxylic acid (2.33 g, 20 mmol) and Et$_3$N (5.6 mL, 40 mmol) in MeOH (40 mL) cooled to 0° C. was added portionwise Boc$_2$O (5.24 g, 24 mmol). The ice bath was removed and the mixture stirred at room temperature for 18 hours. After evaporation of the solvent the resulting oil was dissolved in EtOAc and washed successively with 1 N aqueous HCl and brine. Drying (Na$_2$SO$_4$) and evaporation gave 4.48 g (85%) of a white solid. The N-Boc protected indoline-2-carboxylic acid (4.48 g, 17 mmol) was dissolved in DMF (50 mL) and cesium carbonate (5.54 g, 17 mmol) and benzyl bromide (1.65 mL, 16.2 mmol) were added. The resulting solution was stirred at room temperature for 24 hours. The reaction mixture was diluted with EtOAc and washed with 1 N acqueous HCl, saturated acqueous NaHCO$_3$ and brine. Drying (Na$_2$SO$_4$) and evaporation gave an oil, which was purified by flash chomatography column on silica gel (petroleum ether/ethyl acetate 12:1) to give 5.42 g (95%) of the protected indoline.

To a solution KHMDS (0.5N in toluene, 8 ml, 4 mmol) in THF (6 ml) cooled to −78° C. was added dropwise a solution of the N-Boc protected benzyl indoline-2-carboxylate (706 mg, 2 mmol) in THF (4 ml). The resulting solution was stirred at −40° C. for 1 hour. After cooling down to −78° C., a solution of tert-butyl 3-(bromomethythiophene-2-carboxylate (1.66 g, 6 mmol) in THF (4 ml) was added dropwise. The reaction mixture was allowed to warm-up slowly (5 hours) to room temperature and diluted with EtOAc (100 ml). The organic layer was washed with 1 N acqueous HCl, saturated acqueous NaHCO$_3$ and brine. Drying (Na$_2$SO$_4$) and evaporation gave an oil, which was purified by flash chromatography column on silica gel (petroleum ether/ethyl acetate 8:1) to give 935 mg (85%) of the fully protected alkylated indoline. $^1$H-NMR (DMSO-d$_6$) δ 7.50 (d, J=5.2 Hz, 1H), 7.34 (s, 5H), 7.03 (t, J=8.0 Hz, 1H), 6.91 (d, J=7.3 Hz, 1H), 6.78 (t, J=7.4 Hz, 1H), 6.72 (d, J=5.1 Hz, 1H), 5.25 (d, J=12.7 Hz, 1H), 5.20 (d, J=12.7 Hz, 1H), 4.16 (d, J=14.2 Hz, 1H), 3.70 (d, J=14.2 Hz, 1H), 3.29 (s, 2H), 1.51 (s, 9H), 1.48 (s, 9H); MS m/z 550 (M$^+$+H).

To a solution of the foregoing compound (935 mg, 1.7 mmol) in MeOH (50 ml) was added Pd/C 30% (160 mg). The reaction mixture was stirred at room temperature under hydrogen (atmospheric pressure) for 18 hours. After dilution with EtOAc and filtration a colourless solution was obtained. Evaporation of the solvent gave 781 mg (100%) of the alkylated indoline carboxylic acid (16) as an oil.

iii) (9x)

To a solution of the acid 16 (230 mg, 0.5 mmol), the dipeptide-hydroxyester 15 (200 mg, 0.6 mmol) and HATU (285 mg, 075 mmol) in dichloromethane (5 ml) cooled to 0° C., was added diisopropylethyl amine (0.22 ml, 1.25 mmol). After addition the cooling bath was removed and the mixture stirred at room temperature for three days. The reaction mixture was diluted with EtOAc (100 ml), washed with 1 N acqueous HCl, saturated acqueous NaHCO$_3$ and brine. Drying (Na$_2$SO$_4$) and evaporation gave an oil, which was purified by flash chromatography column on silica gel (petroleum ether/ethyl acetate 2:1) to give 197 mg (53%) of the coupling product as a mixture of 8 diastereomers. $^1$H-NMR (DMSO-d$_6$) δ 7.60–6.56 (m, 7H), 6.10–5.68 (m, 1H), 4.43–3.94 (m, 3H), 3.65–3.54 (m, 3H), 3.44–3.10 (m, 2H), 2.17–1.89 (m, 2H), 1.67–1.40 (m, 18H), 0.90–0.86 (m, 6H); MS m/z 738 (M$^+$+H).

To a solution of the foregoing compound (197 mg, 0.26 mmol) in dichloromethane (4 ml) and $^t$BuOH (4 drops) was added DMP (331 mg, 0.78 mmol) at room temperature. After stirring for 3 hours the reaction mixture was diluted with EtOAc (100 ml), washed with saturated acqueous NaHCO$_3$ and saturated acqueous Na$_2$S$_2$O$_3$ (1:1) and brine. Drying (Na$_2$SO$_4$) and evaporation gave 195 mg of the ketoester as an oil, which was dissolved in TFA/dichloromethane/water (65:30:5) (30 mL) and stirred at room temperature for 3 hours. After evaporation of the solvent an oil was obtained, which was dissolved in methanol (20 mL). Aqueous sodium hydroxide (1 N, 10 mL) was added and the solution stirred at room temperature for 12 min. After addition of hydrochloric acid (1 N, 1 mL), the mixture was diluted with water/acetonitrile (80:20, v/v). The product was isolated by preparative RP-HPLC (Waters Symmetry). Flow 25 mL/min; Gradient linear, 80% A, 2 min isocratic, in 43 min to 60% as the trifluoroacetate.

First fraction: RT: 8.5 min, 12 mg (7%) of a colourless powder after lyophilization; 1 diastereomer. 'H-' NMR (DMSO-ds) δ 8.75 (d, J=6.9 Hz, 1H), 7.82 (d, J=8.3 Hz, 1H), 7.53 (d, J=5.1 Hz, 1H), 7.04 (d, J=5.1 Hz, 1H), 6.86 (br d, J=5.9 Hz, 2H), 8.75 (m, 2H), 6.11 (br t, J=56.0 Hz, 1H), 4.95 (br d, J=3.7 Hz, 1H), 4.34 (br s, 1H), 3.72 (d, J=13.6 Hz, 1H), 3.09 (s, 1H), 2.44–2.13 (m, 3H), 1.42 (br s, 2H), 0.80 (br s, 6H); $^{19}$F-NMR (DMSO-d$_6$) δ −114.9 (d, J=282 Hz), −114.1 (d, J=282 Hz); MS m/z 566 (M$^+$+H).

2. Inhibition of NS3 Protease

The ability of the compounds to inhibit NS3 protease was evaluated using an NS3/4A complex comprising the NS3 protease domain and a modified form of the NS4A peptide, Pep 4AK [KKKGSVVIVGRIILSGR(NH$_2$)]. As substrate, a substrate peptide 4AB [DEMEECASHLPYK] based on the sequence of the NS4A/NS4B cleavage site of the HCV polyprotein, was used.

Cleavage assays were performed in 57 μl 150 mM Hepes pH7.5, 1% CHAPS, 15% glycerol, 10 mM DTT (buffer A), to which 3 μl substrate peptide were added. As protease co-factor a peptide spanning the central hydrophobic core (residues 21–34) of the NS4A protein, Pep4AK [KKKGSVVIVGRIILSGR(NH$_2$)] was used. Buffer solutions containing 80 μM Pep4AK were preincubated for 10 minutes with 10–200 nM protease and reactions were started by addition of substrate. Six duplicate data points at different substrate concentrations were used to calculate kinetic parameters. Incubation times were chosen in order to obtain <7% substrate conversion and reactions were stopped by addition of 40 μl 1% TFA. Cleavage of peptide substrates was determined by HPLC using a Merck-Hitachi chromatograph equipped with an autosampler. 80 μl samples were injected on a Lichrospher C18 reversed phase cartridge column (4×74 mm, 5 μm, Merck) and fragments were separated using a 10–40% acetonitrile gradient a 5%/min using a flow rate of 2.5 ml/min. Peak detection was accomplished by monitoring both the absorbance at 220 nm and tyrosine fluorescence ($\lambda_{ex}$=260 nm, $\lambda_{em}$=305 nm). Cleavage products were quantitated by integration of chromatograms with respect to appropriate standards. Kinetic parameters were calculated from nonlinear least-squares fit of initial rates as a function of substrate concentration with the help of a Kaleidagraph software, assuming Michaelis-Menten kinetics.

$K_i$ values of peptide inhibitors were calculated from substrate titration experiments performed in the presence of increasing amounts of inhibitor. Experimental data sets were simultaneously fitted to eq.1 using a multicurve fit macro with the help of a Sigmaplot software:

$$V=(V_{max}S)/(K_m(1+K_i/I)+S); \qquad (eq.1)$$

Alternatively, $K_i$ values were derived from IC50 values, calculated using a four-parameter logistic function, according to eq.2:

$$IC50=(1+S/K_m)K_i \qquad (eq.2)$$

Results for the compounds synthesized in Examples 1 to 9 above are tabulated below in Tables 1 to 4.

$IC_{50}$ values were determined for a variety of hexapeptides, tetrapeptides, tripeptides, capped dipeptide keto acids and indoline keto acids, and these also are tabulated in Tables 1 to 4, which follow.

In the tables the column headed "isomeric ratio" indicates the diastereomeric ratio of the compounds as tested. In the compounds of Tables 1 and 2 there is only one stereocentre which gives rise to diastereomers, the P1 (difluorinated) amino acid. In this series, the L enantiomer is known to be preferred (see e.g. Table 4, entries 1b, 1c). Thus in Tables 1 and 2, "single" isomer indicates substantially pure diastereomer with L stereochemistry at P1. Where a ratio is given it is that of L to D enantiomer at P1.

The compounds of Tables 3 and 4 have multiple stereocentres. Some compounds were separated to yield a single diastereomer, which was usually more active than the other diastereomers, although those also may have useful activity. Compounds of the indoline series contain three stereocentres, which give rise to eight stereoisomers. No separation was attempted and the mixture was tested as that. All stereoisomers are believed to be present in roughly equal amounts in these mixtures.

TABLE 1

| Entry | Structure | $IC_{50}$ | isomer ratio |
|---|---|---|---|
| 1a | [structure] | 3 | single |
| 1b | [structure] | (L) 20 nM<br>(D) 1 μM | single<br>single |
| 1c | [structure] | (L) 0.5 nM<br>(D) 43 nM | single<br>single |

TABLE 1-continued

| Entry | Structure | IC$_{50}$ | isomer ratio |
|---|---|---|---|
| 1d | 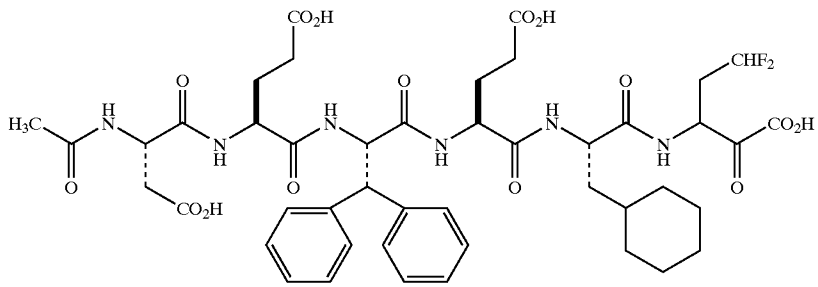 | 0.4 nM | single |
| 1e | 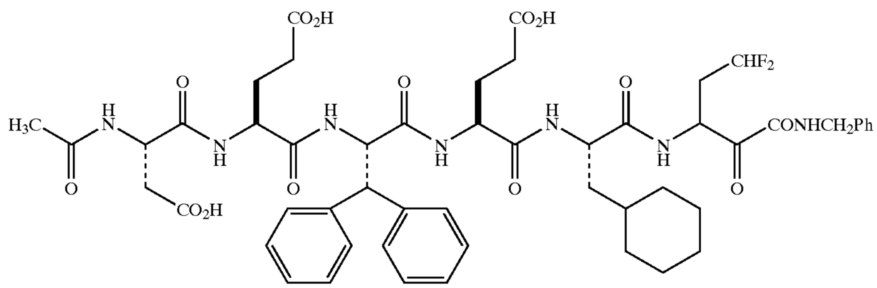 | 5 nM | 2:1 |
| 1f | 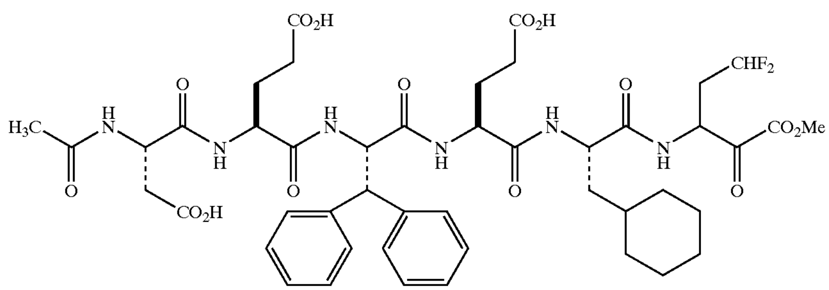 | 800 nM | 1:1 |
| 1g | 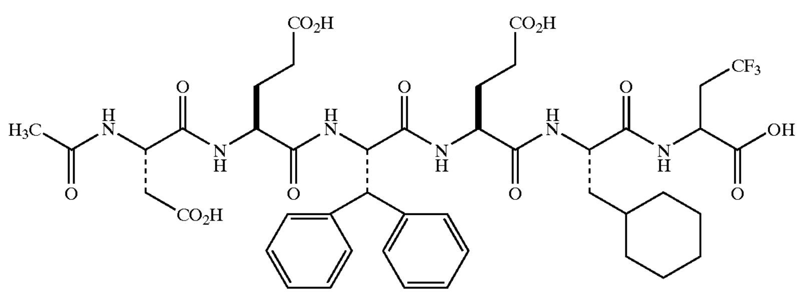 | 100 nM | single |
| 1h | 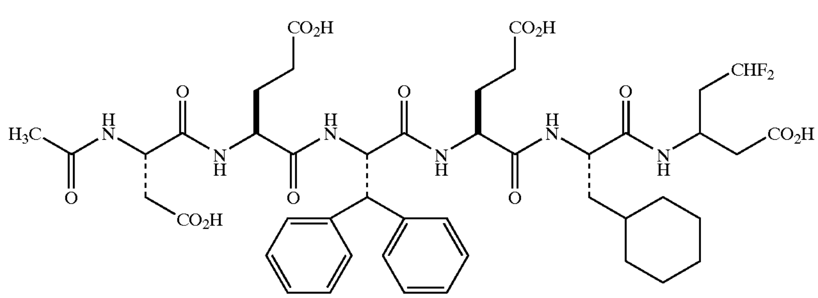 | 3 µM | single |

TABLE 1-continued

| Entry | Structure | IC$_{50}$ | isomer ratio |
|---|---|---|---|
| 1i | 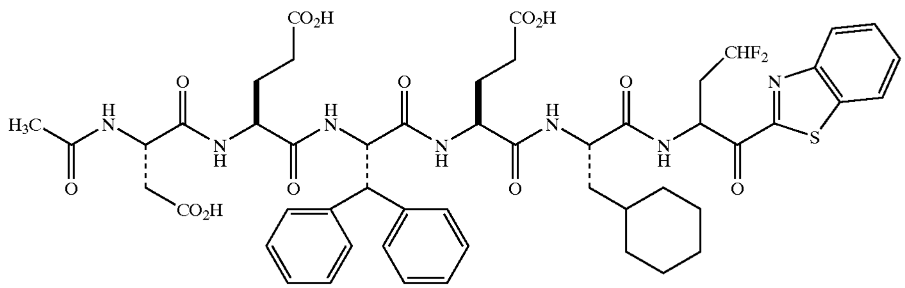 | 150 nM | 1:1 |
| 1j | 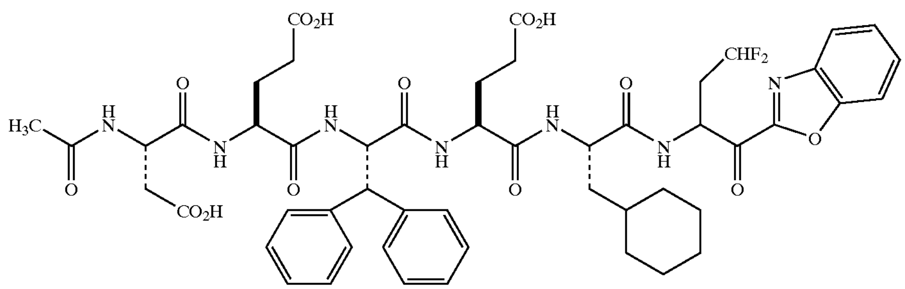 | 600 nM | 1:1 |
| 1k | 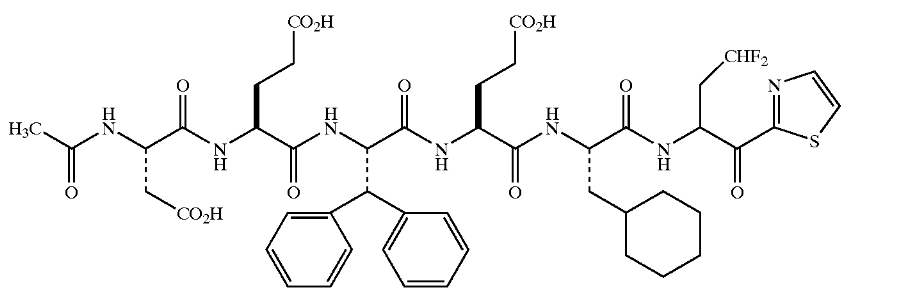 | 1 µM | 3:1 |
| 1l | 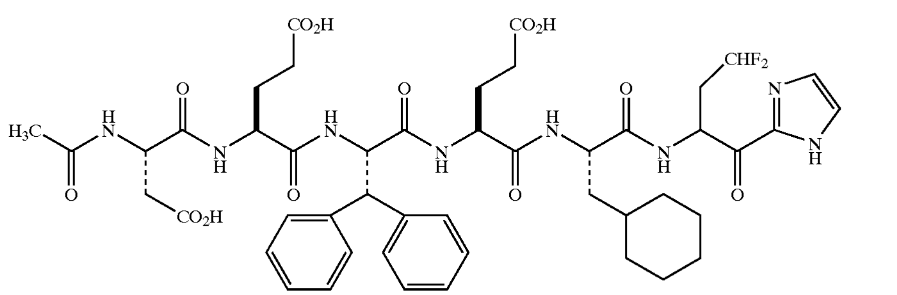 | 6 µM | single |
| 1m | 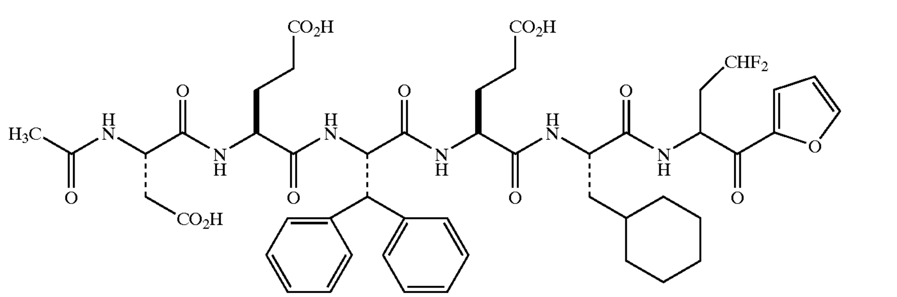 | 7 µM | single |

TABLE 1-continued

| Entry | Structure | IC$_{50}$ | isomer ratio |
|---|---|---|---|
| 1n | 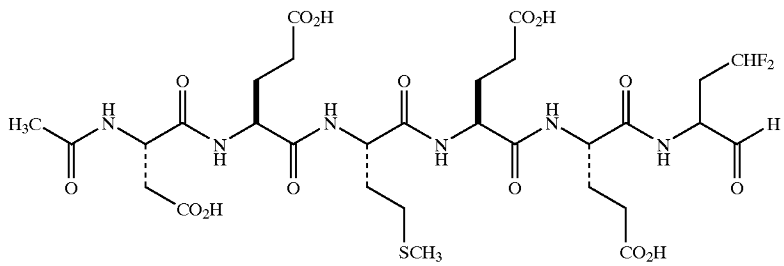 | 148 nM | 1:1 |
| 1o | 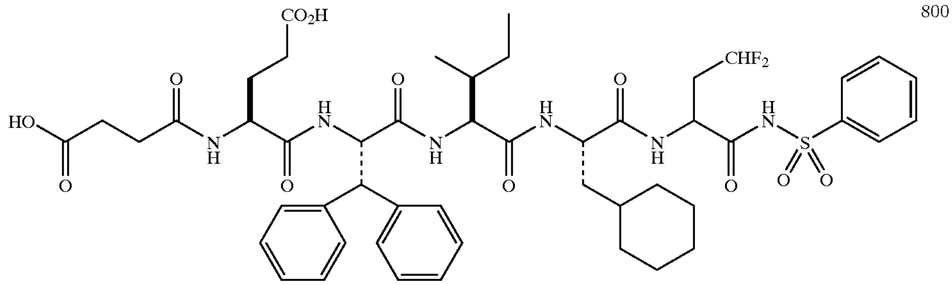 | 800 nM | 2:1 |

TABLE 2

| STRUCTURE | IC50 (µM) | isomer ratio |
|---|---|---|
| 2a | 10 | single |
| 2b | 11.4 | 1:1 |

TABLE 2-continued
| STRUCTURE | IC50 (μM) | isomer ratio |
|---|---|---|
| 2c 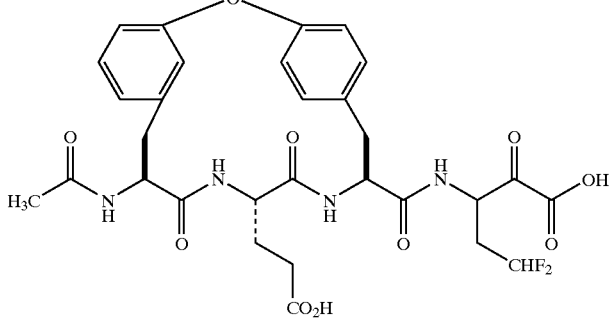 | 47 | single |
| 3a 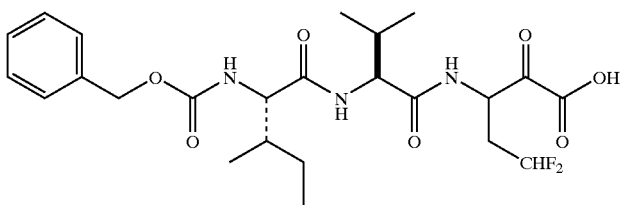 | 16 | 4:1 |
| 3b 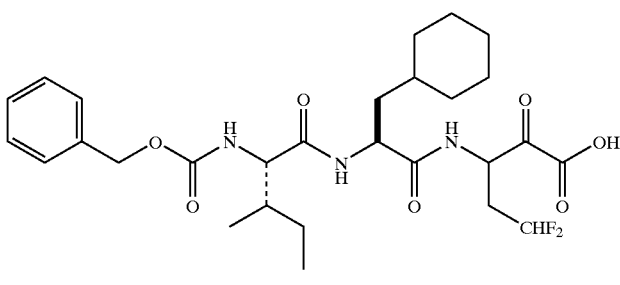 | 1.4 | >10:1 |
| 3c 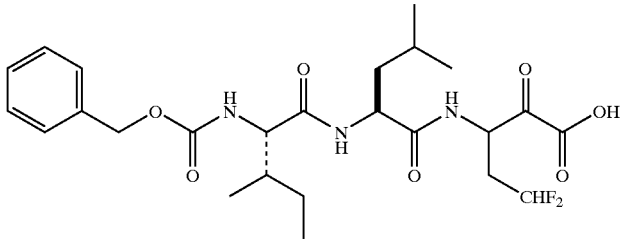 | 1.4 | single |
| 3d 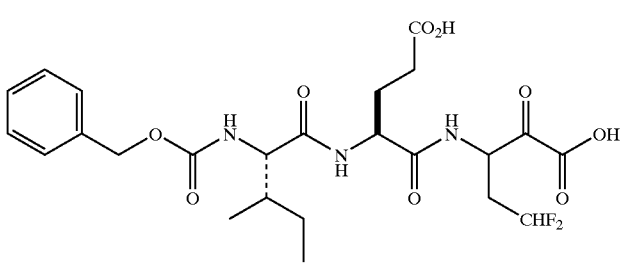 | 9.3 | 2:1 |
| 3e 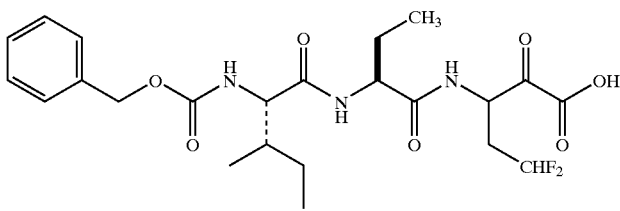 | 3 | single |

TABLE 2-continued

| STRUCTURE | IC50 (μM) | isomer ratio |
|---|---|---|
| 3f | 3 | single |
| 3g | 16 | 6:1 |
| 4a | 6.5 | 1.8:1 |
| 4b | 39 | 3:1 |
| 4c | 1.7 | single |
| 4d | 0.44 | single |

TABLE 2-continued

| STRUCTURE | IC50 (μM) | isomer ratio |
|---|---|---|
| 4e | 7.8 | single |
| 4f | 1 | single |
| 5a | 0.7 | single |
| 5b | 1.2 | single |
| 5c | 1.5 | 9:1 |
| 5d | 0.5 | single |

TABLE 2-continued
| STRUCTURE | IC50 (μM) | isomer ratio |
|---|---|---|
| 5f 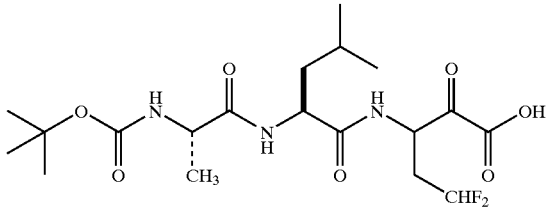 | 8.9 | single |
| 5g 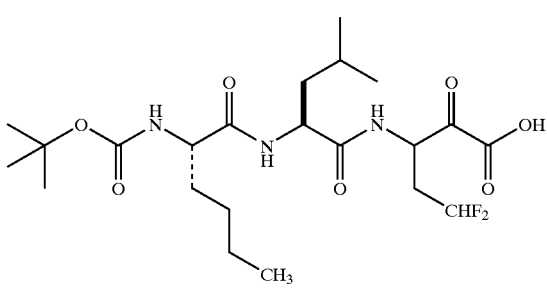 | 1.2 | single |
| 5h 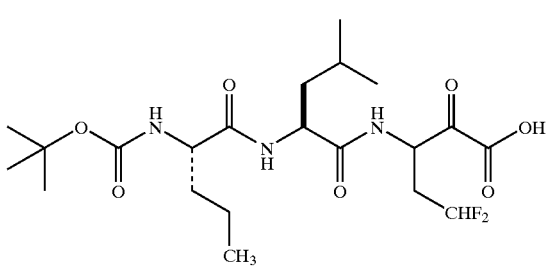 | 1.5 | single |
| 5i 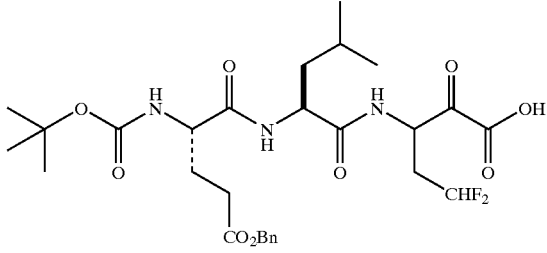 | 5.8 | single |
| 5j 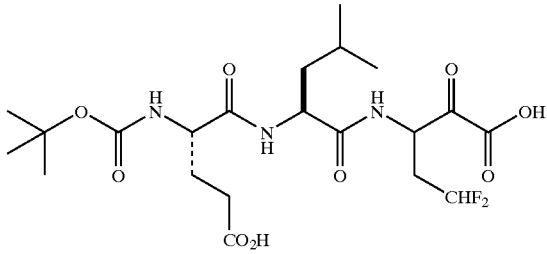 | 0.33 | single |
| 5k 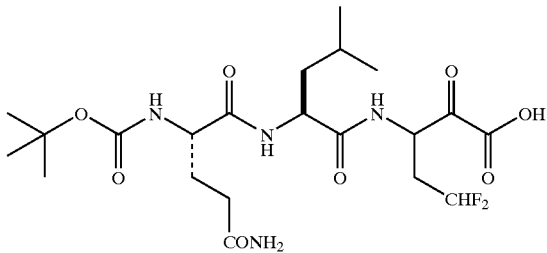 | 2.1 | single |

TABLE 2-continued

| STRUCTURE | IC50 (µM) | isomer ratio |
|---|---|---|
| 5l | 3.5 | single |
| 5m | 1.6 | single |
| 5n | 0.72 | single |
| 5o | 0.3 | >10:1 |
| 5p | 2.4 | >9:1 |
| 5q | 1.6 | >9:1 |

TABLE 2-continued

| STRUCTURE | IC50 (μM) | isomer ratio |
|---|---|---|
| 5r | 5.8 | 9:1 |
| 5s | 3.8 | 4:1 |
| 5t | 2.5 | >10:1 |
| 5u | 0.4 | >10:1 |
| 6a | 26 | >9:1 |

TABLE 2-continued

| STRUCTURE | IC50 (μM) | isomer ratio |
|---|---|---|
| 6b [structure] | 50 | 2:1 |

Compound "1a" refers to a SEQ ID NO: 5 (acetylated at its amino terminus). Compound "1n" refers a SEQ ID NO: 5 (acetylated at its amino terminus) and modified at its carboxyl end by replacing C(O)OH with C(O)H.

TABLE 3

| STRUCTURE | IC50 (μM) | isomer ratio |
|---|---|---|
| 7a [benzyloxy] | 74 | >10:1 |
| 7b [butyl] | 56 | single |
| 7c [3-pentyl/hexyl branched] | 78 | 1.7:1 |
| 7d [HOOC-propyl] | 6 | >10:1 |
| 7e [HOOC-CH2-C(CH3)2-] | 4 | 4:1 |
| 7f [HOOC-C(CH3)2-CH2CH2-] + [HOOC-CH2CH2-C(CH3)2-] | 35 | a) |
| 7g [HO2C-CH2-C(CH3)2-CH2-] + [HO2C-C(CH3)2-CH2-] | 19 | a) |
| 7h [HOOC-CH2-O-CH2-] | 32 | 1.5:1 |
| 7i [Cbz-N(CH2COOH)-CH2-] | 20 | single |

TABLE 3-continued
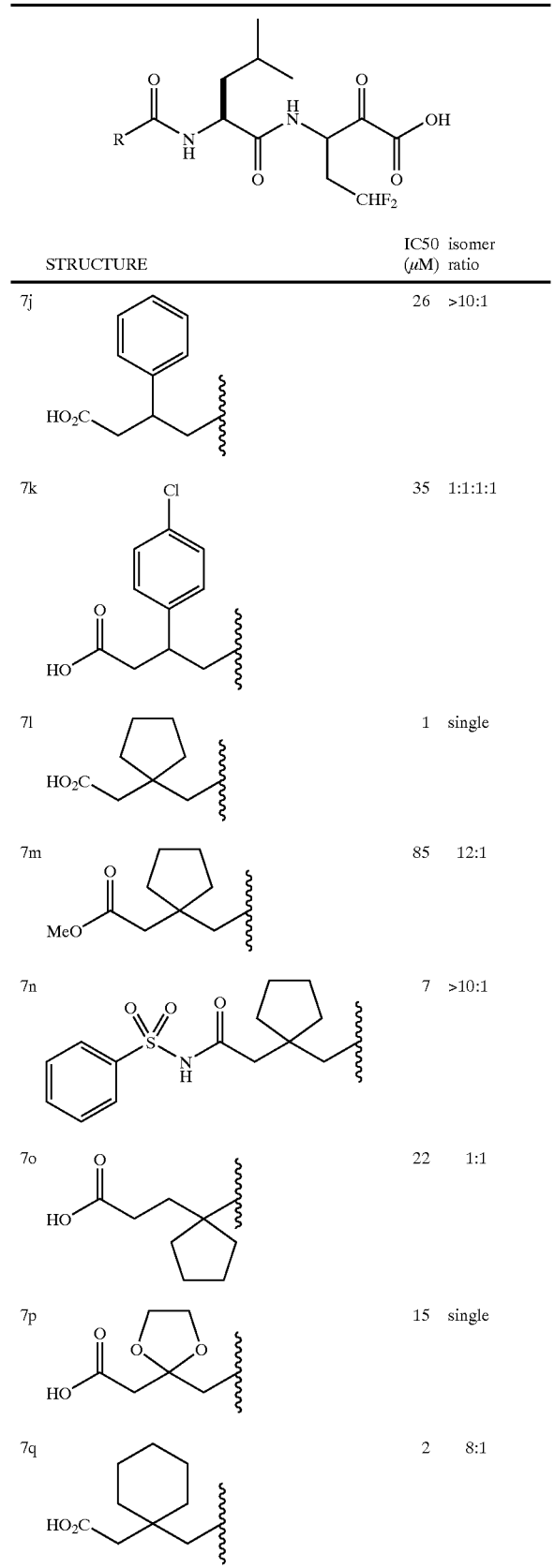
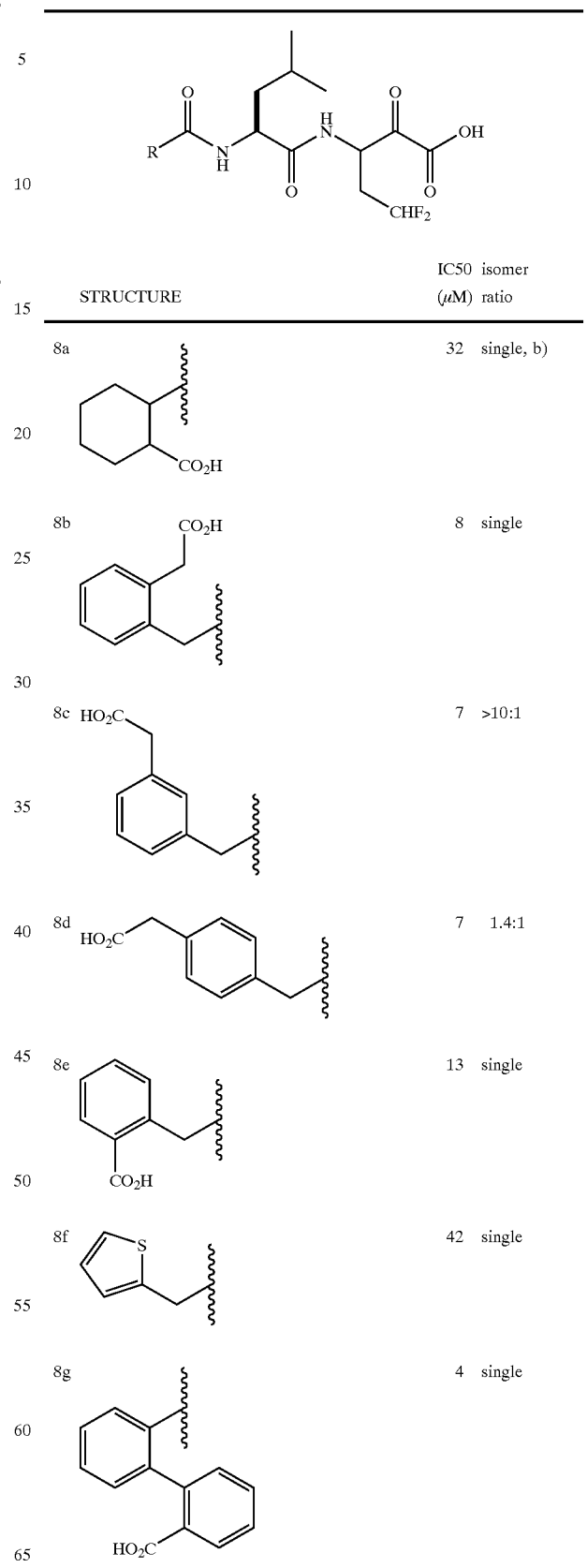

TABLE 3-continued

| STRUCTURE | IC50 (μM) | isomer ratio |
|---|---|---|
| 8h | 6 | single |
| 8i | 28 | 1:1:1:1 |
| 8j | 100 | 1.5:1:1:1 |
| 8k | 72 | 1:1:1:1 |
| 8l | 14 | 1:1 |
| 8m | 60 | c) |
| 8n | 6 | 1:1 |
| 8o | 56 | 1:1 |
| 8p | 25 | 1:1 |
| 8q | 25 | 1:1 |
| 8r | 82 | 1:1 |
| 8s | 18 | single | a) undetermined mixture of regio- and stereoisomers
b) cis-stereochemistry at cyclohexyl ring
c) >10:1 at P1; 1:1 mixture lactone TABLE 4
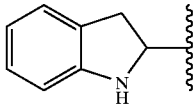
| | STRUCTURE | IC50 (μM) | isomer ratio |
|---|---|---|---|
| 9a | 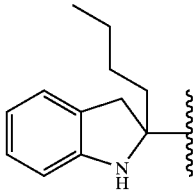 | 50 | single |
| 9b | 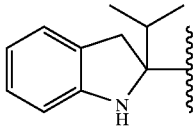 | 87 | 1:1:1 |
| 9c | 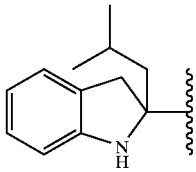 | 92 | 1.5:1:1:1 |
| 9d | 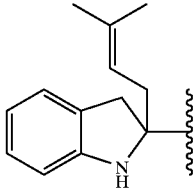 | 16 | 1:1:1 |
| 9e | 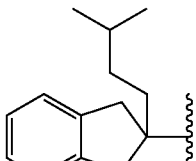 | 69 | 2:2:1:1 |
| 9f | 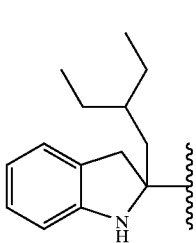 | 120 | 1:1 |
| 9g | 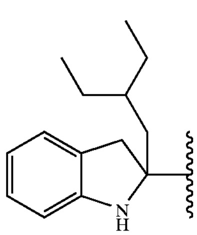 | 15 | single |

TABLE 4-continued

| STRUCTURE | IC50 (μM) | isomer ratio |
|---|---|---|
| 9h | 81 | a) |
| 9i | 20 | single |
| 9j | 34 | 1:1 |
| 9k | 69 | 1:1:1 |
| 9l | 31 | 1:1:1 |
| 9m | 57 | >10:1 |

TABLE 4-continued
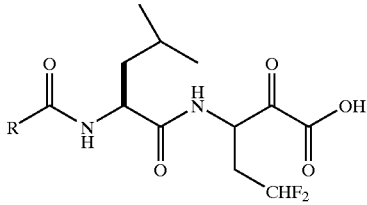
| | STRUCTURE | IC50 (μM) | isomer ratio |
|---|---|---|---|
| 9n | 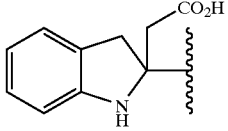 | 81 | 1:1 |
| 9o | 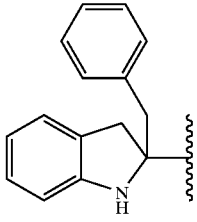 | 45 | 1:1:1:1 |
| 9p | 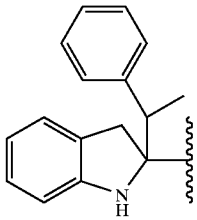 | 88 | a) |
| 9q | 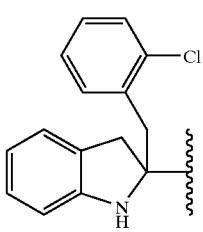 | 5 | single |
| 9r | 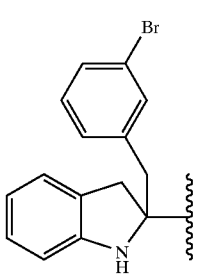 | 100 | 1:1:1:1 |

TABLE 4-continued

| STRUCTURE | | IC50 (μM) | isomer ratio |
|---|---|---|---|
| 9s | OMe, indoline-CH2-(3-methoxyphenyl) | 38 | 2:1:1:1 |
| 9t | CN, indoline-CH2-(3-cyanophenyl) | 9 | 2.7:2:1 |
| 9u | CO2H, indoline-CH2-(3-carboxyphenyl) | 0.8 | >10:1 |
| 9v | OPh, indoline-CH2-(3-phenoxyphenyl) | 24 | 3:1 |
| 9w | Cl, indoline-CH2-(5-chlorothiophen-2-yl) | 3 | 1:1:1 |

TABLE 4-continued
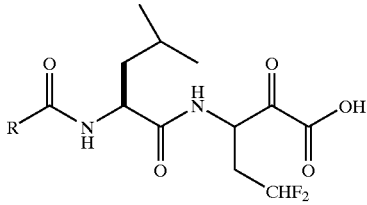
| | STRUCTURE | IC50 (μM) | isomer ratio |
|---|---|---|---|
| 9x | 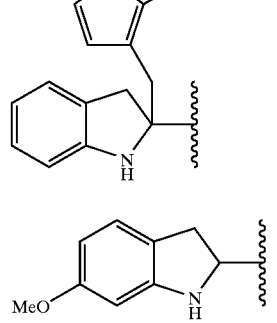 | 0.7 | single |
| 10a | 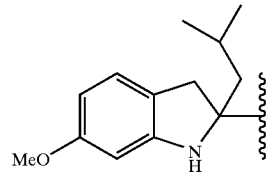 | 25 | single |
| 10b | 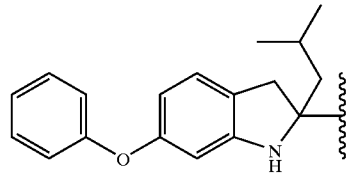 | 24 | single |
| 10c | 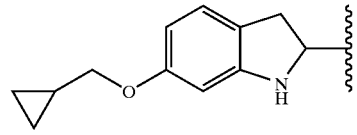 | 100 | 1:1:1:1 |
| 10d | 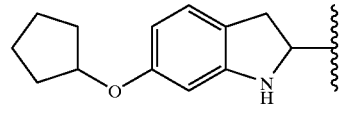 | 66 | >9:1 |
| 10e | 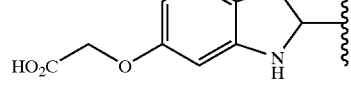 | 18 | single |
| 10f | 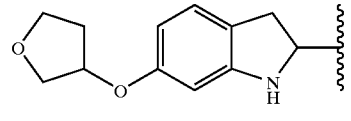 | 10 | single |
| 10g | 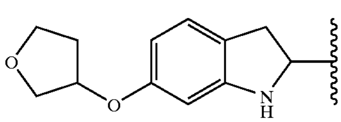 | 23 | 1:1 |

TABLE 4-continued
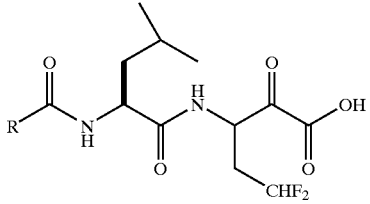
| | STRUCTURE | IC50 (μM) | isomer ratio |
|---|---|---|---|
| 10h | 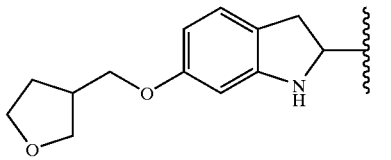 | 16 | 1:1 |
| 10i | 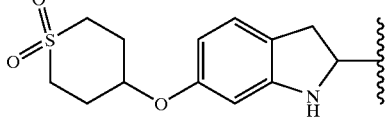 | 30 | single |
| 11 | 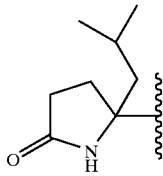 | 43 | 2:1.5:1:1 |
| 12 | 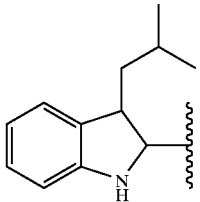 | 26 | single, b) |
| 13 | 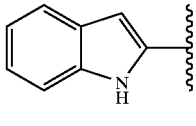 | 70 | single |
| 14 | 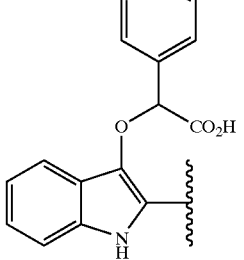 | 10 | single |
a) mixture of eight possible diastereomers, ratio not determined
b) stereochemistry on indoline ring is trans

What is claimed is:

1. A fluorine containing oligopeptide of formula:

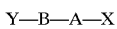   (FORMULA I)

wherein:

A is an amino acid residue of formula:

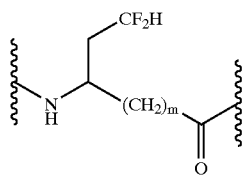

where m is 0,

B is a naturally or non-naturally occurring amino acid residue of formula:

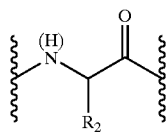

wherein $R_2$ contains from 1 to 20 carbon atoms is a non- polar, or polar but uncharged sidechain or is a side chain containing an acidic functionality;

X is selected from the following:

—$CO_2R_8$; —H; —$OR_8$; —$CF_3$; —$CONR_9R_{10}$; —$CF_2CONR_9R_{10}$; —$NH.SO_2R_{25}$ or a heterocyclic group of formula:

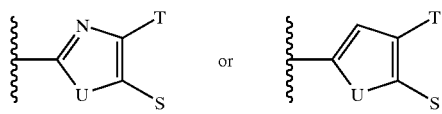

wherein U is sulphur, oxygen or $NR_{11}$; $R_8$, $R_9$, $R_{10}$, $R_{11}$ and $R_{25}$ are, independently, hydrogen or a lower alkyl, lower alkenyl, aryl, or aralkyl group, and S and T are each independently either H or $R_{12}$, where $R_{12}$ is a lower alkyl, lower alkenyl, aryl or aralkyl group, or can together form a ring; and Y is selected from (i) and (ii) below:

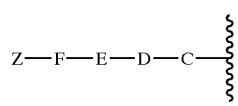  (i)

wherein C is a natural or non-natural amino acid residue having a non-polar, polar but uncharged, or acidic side chain containing from 1 to 20 carbon atoms;

D may be absent, but where present is a natural or non-natural amino acid having a hydrophobic side chain containing 1 to 20 carbon atoms;

E may be absent, but where present is a natural or non-natural amino acid having an acidic side chain containing from 1 to 20 carbon atoms, or is a dicarboxylic acid containing up to 10 carbon atoms;

F may be absent, but where present is a natural or non-natural amino acid having an acidic side chain containing from 1 to 20 carbon atoms, or is a dicarboxylic acid containing up to 10 carbon atoms; and Z may be absent, —H, or a group of formula $R_7CO^-$, where $R_7$ is a group containing from 1 to 20 carbon atoms which is chosen such that the group $R_7CO^-$ together with the nitrogen atom to which it is attached forms an amide, urethane or urea linkage;

  (ii)

where $R_{13}$ is an aliphatic or aromatic group containing from 1 to 25, carbon atoms and 0–5 oxygen atoms, 0–3 nitrogen atoms, 0 to 2 sulphur atoms and up to 9 other heteroatoms which may be the same or different;

or a pharmaceutically acceptable salt or ester thereof.

2. An oligopeptide of Formula I or a salt or ester thereof according to claim 1 wherein X is selected from:

—$CO_2H$, —$CONHCH_2Ph$, —H, —OH, —$NHSO_2R_{25}$ (where $R_{25}$ is as defined in claim 1),

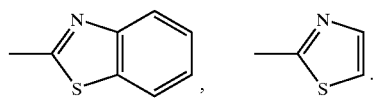

3. An oligopeptide of Formula I or a salt or ester thereof according to claim 2 wherein X is selected from: —H; —OH; —COOH, and —$NHSO_2R_{25}$.

4. An oligopeptide of Formula I or a salt or ester thereof according to claim 3 wherein B is selected from: glutamic acid and aspartic acid, 2-aminobutyric acid, 4,4-difluoro-2-aminobutyric acid, alanine, isoleucine, valine, leucine, cysteine, phenylalanine, naphthylalanine, β-cyclohexylalanine, and proline.

5. An oligopeptide, salt or ester according to claim 4 wherein B is selected from β-cyclohexylalanine, leucine, glutamic acid and 4,4-difluoro-2-aminobutyric acid.

6. An oligopeptide, salt or ester according claim 5 wherein Y is a group of formula:

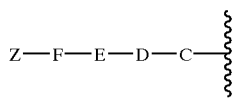

and C is selected from: alanine, isoleucine, leucine, phenylalanine, valine, norleucine, norvaline, glutamic acid, glutamine, aspartic acid, α-t-butyl glycine, α-cinnamylglycine, homoleucine, 3,5 dichlorophenylalanine, 2-thienylalanine, 3-bromophenylalanine and α-cyclopentyl glycine.

7. An oligopeptide, salt or ester according to claim 6 wherein C is selected from: isoleucine, glutamic acid, α-cyclopentylglycine, t-butyl glycine and valine.

8. An oligopeptide, salt or ester according to claim 7 wherein D is selected from: methionine, isoleucine, leucine, norleucine, valine, methyl valine, phenylglycine or diphenylalanine.

9. An oligopeptide, salt or ester according to claim 8 wherein D is leucine or diphenylalanine.

10. An oligopeptide, salt or ester according to claim 8 wherein E is selected from glutamic acid, aspartic acid, succinic acid and glutaric acid.

11. An oligopeptide, salt or ester according to claim 10 wherein F is selected from glutamic acid, aspartic acid, succinic acid and glutaric acid.

12. A tripeptide of formula:

Z—C—B—A—X'' in which A, B, C and Z are as defined in claim 1 and X'' is a carboxylic acid group (—CO$_2$H), amide group (—CONR$_9$R$_{10}$) or hydrogen; or a pharmaceutically acceptable salt or ester thereof.

13. A fluorine containing dipeptide according to Formula I of claim 1 wherein:

X is —COOH;

B is leucine; and

Y is a group of formula R$_{13}$CO— where R$_{13}$, is as defined in claim 1; or a pharmaceutically acceptable salt or ester thereof.

14. A dipeptide, salt, or ester according to claim 13 wherein R$_{13}$ is a group of general;

$$HO-\overset{O}{\underset{\|}{C}}-\left[\underset{R_a}{\overset{R_a}{\diagdown\diagup}}C\right]_{2-6}$$

wherein each R$_a$ is independently selected from hydrogen, lower alkyl, lower alkenyl, lower alkoxy, optionally substituted aryl or aralkyl groups or two R$_a$ taken together result in the formation of a three to seven membered aliphatic or aromatic ring which optionally contains at least one heteroatom.

15. A dipeptide, salt or ester according to claim 14 wherein at least one group —C(R$_a$)$_2$— is replaced by —O—.

16. A dipeptide, salt or ester according to claim 14 wherein R$_{13}$ is a group of formula:

$$HO-\overset{O}{\underset{\|}{C}}-(CH_2)_{0,1}-\left[\text{phenyl}-\text{phenyl}\right]_{0,1}-(CH_2)_{0,1}-$$

17. A dipeptide salt or ester according to claim 13 wherein R$_{13}$ is a group of formula:

$$R_{14}-\underset{CH}{\overset{}{\diagdown\diagup}}$$

where R$_{14}$ is a cycloalkyl or optionally substituted aryl group.

18. A dipeptide salt or ester according to claim 13 wherein R$_{13}$ is a group selected from:

(a)

[indoline structure with R$_{16}$ and R$_{15}$]

where R$_{15}$ is hydrogen, an optionally branched, optionally interrupted and optionally substituted lower alkyl or lower alkenyl group or an optionally substituted aralkyl group, R$_{16}$ is hydrogen or an optionally substituted and optionally interrupted lower alkoxy or aryloxy-group;

(b)

[pyrrolidinone structure with R$_{15}$]

where R$_{15}$ is as defined above; and (c)

[indole structure with R$_{17}$, R$_{18}$, R$_{19}$]

where each of R$_{17}$, R$_{18}$ and R$_{19}$, independently, is selected from hydrogen, optionally substituted lower alkyl, lower alkenyl and lower alkoxy, optionally substituted aryl, aralkyl, aryoxy or aralkoxy, a carboxylic acid group optionally as its lower alkyl ester, a halogen, cyano, or CF$_3$ group.

19. A dipeptide salt or ester according to claim 17, wherein R$_{13}$ is a group of the formula $$R_{14}-\underset{OH}{\overset{}{\diagdown\diagup}}$$

20. An oligopeptide, salt or ester according to claim 11, wherein X is either —H; —OH; or —COOH.

21. An oligopeptide according to claim 1, or a salt or ester thereof, wherein said oligopeptide has the following structure:

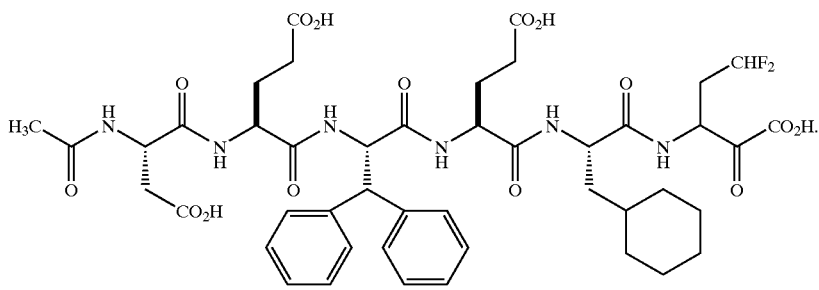

22. A pharmaceutical composition comprising a fluorine containing oligopeptide, salt or ester according to claim 1 and a pharmaceutically acceptable excipient, diluent or carrier.

23. A pharmaceutical composition comprising a fluorine containing oligopeptide, salt or ester according to claim 4 and a pharmaceutically acceptable excipient, diluent or carrier.

24. A pharmaceutical composition comprising a fluorine containing oligopeptide, salt or ester according to claim 6 and a pharmaceutically acceptable excipient, diluent or carrier.

25. A pharmaceutical composition comprising a fluorine containing oligopeptide, salt or ester according to claim 11 and a pharmaceutically acceptable excipient, diluent or carrier.

26. A pharmaceutical composition comprising a fluorine containing oligopeptide, salt or ester according to claim 20 and a pharmaceutically acceptable excipient, diluent or carrier.

27. A method of inhibiting Hepatitis C virus (HCV) NS3 protease activity, and/or of treating or ameliorating HCV infection comprising administering to a human or animal subject, a therapeutically or prophylactically effective amount of a composition according to claim 22.

28. A method of inhibiting Hepatitis C virus (HCV) NS3 protease activity, and/or of treating or ameliorating HCV infection comprising administering to a human or animal subject, a therapeutically or prophylactically effective amount of a composition according to claim 24.

29. A method of inhibiting Hepatitis C virus (HCV) NS3 protease activity, and/or of treating or ameliorating HCV infection comprising administering to a human or animal subject, a therapeutically or prophylactically effective amount of a composition according to claim 26.

* * * * *

UNITED STATES PATENT AND TRADEMARK OFFICE
CERTIFICATE OF CORRECTION

PATENT NO. : 6,867,284 B1
DATED : March 15, 2005
INVENTOR(S) : Matassa, V. et al.

It is certified that error appears in the above-identified patent and that said Letters Patent is hereby corrected as shown below:

Column 87,
Line 17, delete "where m is 0," and insert -- where m is 0 or 1 --.

Column 90,
Line 50, delete "aryoxy" and insert -- aryloxy --.

Signed and Sealed this

Seventh Day of June, 2005

JON W. DUDAS
*Director of the United States Patent and Trademark Office*